(12) United States Patent
Qin et al.

(10) Patent No.: US 7,195,916 B2
(45) Date of Patent: Mar. 27, 2007

(54) METHOD FOR EXPRESSION OF SMALL ANTIVIRAL RNA MOLECULES WITHIN A CELL

(75) Inventors: Xiao-Feng Qin, Pasadena, CA (US); David Baltimore, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 501 days.

(21) Appl. No.: 10/319,341

(22) Filed: Dec. 12, 2002

(65) Prior Publication Data

US 2003/0157691 A1    Aug. 21, 2003

Related U.S. Application Data

(63) Continuation-in-part of application No. 10/243,553, filed on Sep. 13, 2002.

(60) Provisional application No. 60/406,436, filed on Aug. 27, 2002, provisional application No. 60/389,592, filed on Jun. 18, 2002, provisional application No. 60/347,782, filed on Jan. 9, 2002, provisional application No. 60/322,031, filed on Sep. 13, 2001.

(51) Int. Cl.
| | |
|---|---|
| C12Q 1/68 | (2006.01) |
| C12P 19/34 | (2006.01) |
| C12N 15/87 | (2006.01) |
| C07H 21/02 | (2006.01) |
| C07H 21/04 | (2006.01) |

(52) U.S. Cl. .................... 435/465; 435/6; 435/91.1; 435/320.1; 435/457; 435/475; 435/489; 536/23.1; 536/24.32; 536/24.5

(58) Field of Classification Search ............. 435/91.1, 435/91.31, 375, 455, 459, 6, 456, 457, 475, 435/489, 235.1, 320.1; 536/23.1, 24.5, 24.32; 514/44
See application file for complete search history.

(56) References Cited

U.S. PATENT DOCUMENTS

| | | | |
|---|---|---|---|
| 5,650,309 A | 7/1997 | Wong-Stall et al. | |
| 5,883,081 A | 3/1999 | Kraus et al. | |
| 6,060,317 A | 5/2000 | Malech | |
| 6,096,538 A | 8/2000 | Kingsman | |
| 6,218,186 B1 | 4/2001 | Choi et al. | |
| 6,255,071 B1 | 7/2001 | Beach et al. | |
| 6,274,788 B1 | 8/2001 | Kumar | |
| 6,312,956 B1 | 11/2001 | Lane | |
| 6,506,559 B1 | 1/2003 | Fire | |
| 6,566,083 B1 | 5/2003 | Thastrup | |
| 6,586,208 B2 | 7/2003 | Donahue | |
| 6,635,472 B1 * | 10/2003 | Lauermann | 435/320.1 |
| 6,664,107 B1 | 12/2003 | Mak | |
| 2003/0124513 A1 * | 7/2003 | McSwiggen | 435/5 |

OTHER PUBLICATIONS

Banerjea Akhil et al., "Inhibition of HIV-1 by lentiviral vector-transduced siRNAs in T lymphocytes differentiated in SCID-hu mice and CD34+ progenitor cell-derived macrophages", Molecular Therapy : The Journal of American Society of Gene Therapy, Jul. 2003, pp. 62-71, vol. 8, No. 1.
Barton G M et al., "Retroviral delivery of small interfering RNA into primary cells", Proceeding of the National Academy of Sciences of USA, Nov. 12, 2002, pp. 14943-14945, vol. 99, No. 23, Washington, USA.
Brummelkamp T R, et al., "A system for Stable Expression of Short Interfering RNAs in Mammalian Cells," Science, Apr. 19, 2002, vol. 296.
Caplen N J et al., "Specific inhibition of gene expression by small double-stranded RNAs in invertebrate and vertebrate systems," PNAS, Aug. 14, 2001, vol. 98, No. 17.
Czauderna Frank et al., "Inducible shRNA expression for application in a prostate cancer mouse model", Nucleic Acids Research, Nov. 1, 2003, p. e127, vol. 31, No. 21.
Devroe E. & Silver P A, "Retrovirus-delivered siRNA", BMC Technology, Aug. 28, 2002, pp. 1-5.
Howard Hughes Medical Institute, "Pushing the Envelope" Nov. 21, 1997.
Jacque J-M et al., "Modulation of HIV-1 replication by RNA interference", Nature, Jul. 25, 2002, pp. 435-438, vol. 418, No. 6896, London Great Britton.
Lawrence D "RNAi could hold promise in the treatment of HIV," The Lancet, vol. 359, Jun. 8, 2002.
Lee N S et al., "Expression of small interfering RNAs targeted against HIV-1 rev transcripts in human cells", Nature Biotechnology, May 2002, pp. 500-505, vol. 19.
Li et al., "Inhibition of HIV-1 infection by lentiviral vectors expressing pol III-promoted anti-HIV RNAs", Molecular Therapy, Academic Press, Aug. 2003, pp. 196-206, vol. 8, No. 2, San Diego, CA, USA.
Lois Carlos et al., "Germline transmission and tissue-specific expression of transgenes delivered by lentiviral vectors", Science, Feb. 1, 2002, pp. 868-872, vol. 295, No. 5556.
Martinez L J, "Katy, bar the door! HIV entry inhibitors," Research/ Initiative/Treatment Action! Jun. 2000.

(Continued)

*Primary Examiner*—Jane Zara
(74) *Attorney, Agent, or Firm*—Knobbe Martens Olson & Bear LLP

(57) ABSTRACT

In one aspect, the invention provides methods and compositions for the expression of small RNA molecules within a cell using a retroviral vector. The methods can be used to express double stranded RNA complexes. Small interfering RNA (siRNA) can be expressed using the methods of the invention within a cell, that interfere with a viral life cycle by down regulating either the viral genome, a viral genome transcript, or a host cell that. In another aspect the invention provides methods for treating patients having suffering from infection, particularly infection with HIV. In a further aspect, the invention provides methods for producing siRNA encoding lentivirus where the siRNA activity may interfere with the lentiviral life cycle.

17 Claims, 13 Drawing Sheets

OTHER PUBLICATIONS

Matsukura S et al., "Establishment of conditional vectors for hairpin siRNA knockdowns", Nucleic Acids Research, Aug. 1, 2003, pp. e77-1, vol. 31, No. 15, Oxford University.

Miyagishi M et al., "U6 promoter-driven simas with four uridine 3' overhangs efficiently suppress targeted gene expression in mammalian cells", Nature Biotechnology, May 2002, pp. 497-500, vol. 19, No. 5, US.

Miyoshi H. et al. "Development of a self-inactivating lentivirus vector", Journal of Virology, 1998, pp. 8150-8157, vol. 72, No. 10.

Naldini, L. et al., "*In Vivo* Delivery and Stable Transduction of Nondividing Cells by a Lentiviral Vector" Science, vol. 272, Apr. 12, 1996.

National Cancer Institute, "Scientists Suggest New Approaches for Development of AIDS Drugs and Vaccines" Charity Wire, Jun. 21, 1999.

Novina C D et al., "siRNA directed inhibition of HIV-1 infection", Nature Medicine, Jul. 2002, pp. 681-686, vol. 8, No. 7.

Ohkawa J. et al., "Control of the functional activity of an antisense RNA by a tetracycline-responsive derivative of the human U6 snRNA promoter", Human Gene Therapy, Mar. 1, 2000, pp. 577-585, vol. 11, No. 4.

Paddison P J et al., "Short hairpin RNAs (shRNAs) induce sequence-specific silencing in mammalian cells" Genes & Development 16:948-958 Mar. 8, 2002.

Paul C P et al., "Effective expression of small interfering RNA in human cells", Nature Biotechnology, May 2002, vol. 20, No. 5, US.

Pomerantz R J, "RNA interference meets HIV-1: Will silence be golden?" Nature Medicine, Jul. 2002, vol. 8, No. 7.

Qin X-F et al., "Inhibiting HIV-1 infection in human T cells by lentiviral-mediated delivery of small interfering RNA against CCR5", Proceeding of the National Academy of Sciences of USA, Jan. 7, 2003, pp. 183-188, vol. 100, No. 1, Washington, USA.

Shankar P, "RNAi-Medicated Inhibition of HIV-1 Replication in Primary Macrophages" Center for Blood Research Boston.

Sirven A et al., "The human immunodeficiency virus type-1 central DNA flap is a crucial determinant for lentiviral vector nuclear import and gene transduction of human hematopoietic stem cells", W.B. Saunders Company, Dec. 15, 2000, pp. 4103-4110, vol. 96, No. 13, Orlando, Florida.

Sui G et al., "A DNA vector-based RNAi technology to suppress gene expression in mammalian cells", Proceeding of the National Academy of Sciences of USA, Apr. 16, 2002, pp. 5515-5520, vol. 99, No. 8, Washington, USA.

University of Pennsylvania Health System: News and Periodicals, "Mutant Gene Products Strong Natural Resistance to HIV-1 Infection in 1 in 100 People," Aug. 8, 1996.

Van De Wetering Marc et al., "Specific Inhibition of gene expression using a stably integrated, inducible small-interfering-RNA vector", EMBO Reports, Jun. 2003, pp. 609-615, vol. 4, No. 6.

Yu Jenn-Yah et al., "RNA interference by expression of short-interfering RNAs and hairpin RNAs in mammalian cells", Proceeding of the National Academy of Sciences of USA, Apr. 30, 1002, pp. 6047-6052, vol. 99, No. 9, Washington, USA.

Zennou V et al., "HIV-1 Genome Nuclear Import is Mediated by a Central DNA Flap," Cell, Apr. 14, 2000, vol. 101, 173-185.

Zufferey R et al., "Woodchuck hepatitis virus posttranscriptional regulatory element enhances expression of transgenes delivered by retroviral vectors", Journal of Virology, 1999, pp. 2886-2892, vol. 74, No. 4.

Arendt et al., "Vector Systems for the Delivery of Small Interfering RNAs: Managing the RISC**" ChemBioChem 2003, 4, pp. 1129-1136.

Lieberman et al., "Interfering with disease: opportunities and roadblocks to harnessing RNA interference," Trends in Molecular Medicine, vol. 9, No. 9 Sep. 2003, pp. 397-403.

Yang Shi, "Mammalian RNAi for the masses," Trends in Genetics, vol. 19, No. 1, Jan. 2003, pp. 9-12.

Brummelkamp et al., "A system for stable expression of short interfering RNAs in mammalian cells." Apr. 19, 2002, vol. 296, pp. 550-553.

Chatterjee et al. "Dual-target inhibition of HIV-1 in virto by means of an adeno-associated antisense vector." Science, Nov. 27, 1992, vol. 258, pp. 1485-1488.

Ilves et al. "Retroviral Vectors designed for targeted expression of RNA polymerases III-driven transcripts: a comparative study." Gene. 1996. vol. 171, pp. 203-208.

Iwakuma et al., Self-inactivating lentilviral vectors with U3 and U5 modifications. Virology. 1999. vol. 261, pp. 120-132.

Junker et al. "Reduction in replication of the human immunodeficiency virus type I in human T cell lines by polymerase III-driven transcription of chimeric tRNA-antisense RNA genes." Antisense Research and Development. 1994, vol. 4, pp. 165-172.

Mummidi et al., "The human CC chemokine Receptor 5 (CCR5) gene" Jour. Biol. Chem., Dec. 5, 1997, vol. 272, p. 30662, col. 2, lines 11-13.

Reiser et al., "Development of Multigene and Regulated Lentivirus Vectors." Jour. Viirol. Nov. 2000, vol. 74, No. 22, pp. 10589-10599.

Timmons et al., "Specific interference by ingested dsRNA." Nature. Oct. 29, 1998, vol. 395, p. 854.

Carmell et al., "The Argonaute family: tentacles that reach into RNAi, developmental control, stem cell maintenance, and tumorigenesis", Genes & Development, 2002, pp. 2733-2742.

Filipowicz et al., "Post-transcriptional gene silencing by siRNAs and miRNAs", Structural Biology, 2005, pp. 331-341.

* cited by examiner

SEQUENCE LISTING

<160> NUMBER OF SEQ ID NOS: 12

<210> SEQ ID NO 1
<211> LENGTH: 56
<212> TYPE: DNA
<213> ORGANISM: Artificial Sequence
<220> FEATURE:
<223> OTHER INFORMATION: This represents an anti-human specific siRNA
      cassette comprising human sequence and synthetic
      linker, loop and terminator sequences.

<400> SEQUENCE: 1
accgagcatg actgacatct acttcaagag agtagatgtc agtcatgctc tttttc     56

<210> SEQ ID NO 2

```
<211> LENGTH: 60
<212> TYPE: DNA
<213> ORGANISM: Artificial Sequence
<220> FEATURE:
<223> OTHER INFORMATION: This represents an anti-human immune deficiency
      virus specific siRNA cassette comprising human
      immune deficiency virus sequence and synthetic
      linker, loop and terminator sequences.

<400> SEQUENCE: 2
gatccccgaa ggtggagaga gagacattca agagatgtct ctctctccac cttcttttc      60

<210> SEQ ID NO 3
<211> LENGTH: 9941
<212> TYPE: DNA
<213> ORGANISM: Artificial Sequence
<220> FEATURE:
<223> OTHER INFORMATION: This sequence represents a lentiviral vector
      comprising a human immunodeficiency virus flap
      sequence, a green fluorescent protein variant
      sequence, a human ubiquitin promoter sequence and
      a woodchuck hepatitis regulator element sequence.

<400> SEQUENCE: 3
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtattac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
```

```
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aagggggat    2460 tgggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agggtgcagc ggcctccgcg ccgggttttg gcgcctcccg    2640
cgggcgcccc cctcctcacg gcgagcgctg ccacgtcaga cgaagggcgc aggagcgttc    2700
ctgatccttc cgcccggacg ctcaggacag cggcccgctg ctcataagac tcggccttag    2760
aaccccagta tcagcagaag gacattttag gacgggactt gggtgactct agggcactgg    2820
ttttctttcc agagagcgga acaggcgagg aaaagtagtc ccttctcggc gattctgcgg    2880
agggatctcc gtggggcggt aacgccgat gattatataa ggacgcgccg ggtgtggcac    2940
agctagttcc gtcgcagccg ggatttgggt cgcggttctt gtttgtggat cgctgtgatc    3000
gtcacttggt gagttgcggg ctgctgggct ggccggggct ttcgtggccg ccgggccgct    3060
cggtgggacg gaagcgtgtg gagagaccgc caagggctgt agtctgggtc cgcgagcaag    3120
gttgccctga actgggggtt ggggggagcg cacaaaatgg cggctgttcc cgagtcttga    3180
atggaagacg cttgtaaggc gggctgtgag gtcgttgaaa caaggtgggg gcatggtgg    3240 gcggcaagaa cccaaggtct tgaggccttc gctaatgcgg gaaagctctt attcgggtga    3300
gatgggctgg ggcaccatct ggggacccty acgtgaagtt tgtcactgac tggagaactc    3360
gggtttgtcg tctggttgcg ggggcggcag ttatgcggtg ccgttgggca gtgcacccgt    3420
acctttggga gcgcgcgcct cgtcgtgtcg tgacgtcacc cgttctgttg cttataatg    3480 cagggtgggg ccacctgccg gtaggtgtgc ggtaggcttt ctccgtcgc aggacgcagg    3540 gttcgggcct agggtaggct ctcctgaatc gacaggcgcc ggacctctgg tgagggagg    3600 gataagtgag gcgtcagttt cttggtcgg ttttatgtac ctatcttctt aagtagctga    3660
agctccggtt ttgaactatg cgctcgggt tggcgagtgt gttttgtgaa gttttttagg    3720
caccttttga aatgtaatca tttggtcaa tatgtaattt tcagtgttag actagtaaag    3780
cttctgcagg tcgactctag aaaattgtcc gctaaattct ggccgttttt ggcttttttg    3840
ttagacagga tccccgggta ccggtcgcca ccatggtgag caaggggcag gagctgttca    3900
ccggggtggt gcccatcctg gtcgagctgg acggcgacgt aaacggccac aagttcagcg    3960
```

```
tgtccggcga gggcgagggc gatgccacct acggcaagct gaccctgaag ttcatctgca    4020
ccaccggcaa gctgcccgtg ccctggccca ccctcgtgac caccctgacc tacggcgtgc    4080
agtgcttcag ccgctacccc gaccacatga agcagcacga cttcttcaag tccgccatgc    4140
ccgaaggcta cgtccaggag cgcaccatct tcttcaagga cgacggcaac tacaagaccc    4200
gcgccgaggt gaagttcgag ggcgacaccc tggtgaaccg catcgagctg aagggcatcg    4260
acttcaagga ggacggcaac atcctggggc acaagctgga gtacaactac aacagccaca    4320
acgtctatat catggccgac aagcagaaga cggcatcaa ggtgaacttc aagatccgcc    4380
acaacatcga ggacggcagc gtgcagctcg ccgaccacta ccagcagaac cccccatcg    4440
gcgacggccc cgtgctgctg cccgacaacc actacctgag cacccagtcc gccctgagca    4500
aagaccccaa cgagaagcgc gatcacatgg tcctgctgga gttcgtgacc gccgccggga    4560
tcactctcgg catggacgag ctgtacaagt aaagcggccg cgactctaga attcgatatc    4620
aagcttatcg ataatcaacc tctggattac aaaatttgtg aaagattgac tggtattctt    4680
aactatgttg ctccttttac gctatgtgga tacgctgctt taatgccttt gtatcatgct    4740
attgcttccc gtatggcttt cattttctcc tccttgtata atcctggtt gctgtctctt    4800
tatgaggagt tgtggcccgt tgtcaggcaa cgtggcgtgg tgtgcactgt gtttgctgac    4860
gcaaccccca ctggttgggg cattgccacc acctgtcagc tcctttccgg gactttcgct    4920
ttcccctcc ctattgccac ggcggaactc atcgccgcct gccttgcccg ctgctggaca    4980
ggggctcggc tgttgggcac tgacaattcc gtggtgttgt cggggaaatc atcgtccttt    5040
ccttggctgc tcgcctgtgt tgccacctgg attctgcgcg gacgtccttc tgctacgtc     5100
ccttcggccc tcaatccagc ggaccttcct tcccgcggcc tgctgccggc tctgcggcct    5160
cttccgcgtc ttcgccttcg ccctcagacg agtcggatct ccctttgggc cgcctccccg    5220
catcgatacc gtcgacctcg agacctagaa aaacatggag caatcacaag tagcaataca    5280
gcagctacca atgctgattg tgcctggcta aagcacaag aggaggagga ggtgggtttt    5340
ccagtcacac ctcaggtacc tttaagacca atgacttaca aggcagctgt agatcttagc    5400
cactttttaa aagaaagggg gggactggaa gggctaattc actcccaacg aagacaagat    5460
atccttgatc tgtggatcta ccacacacaa ggctacttcc ctgattggca gaactacaca    5520
ccagggccag ggatcagata tccactgacc tttggatggt gctacaagct agtaccagtt    5580
gagcaagaga aggtagaaga agccaatgaa ggagagaaca cccgcttgtt acaccctgtg    5640
agcctgcatg ggatggatga cccggagaga gaagtattag agtggaggtt tgacagccgc    5700
ctagcatttc atcacatggc ccgagagctg catccggact gtactgggtc tctctggtta    5760
gaccagatct gagcctggga gctctctggc taactaggga acccactgct taagcctcaa    5820
taaagcttgc cttgagtgct tcaagtagtg tgtgcccgtc tgttgtgtga ctctggtaac    5880
tagagatccc tcagaccctt ttagtcagtg tggaaaatct ctagcagggc cgtttaaac     5940
ccgctgatca gcctcgactg tgccttctag ttgccagcca tctgttgttt gcccctcccc    6000
cgtgccttcc ttgaccctgg aaggtgccac tcccactgtc ctttcctaat aaaatgagga    6060
aattgcatcg cattgtctga gtaggtgtca ttctattctg ggggtgggg tgggcagga     6120
cagcaagggg gaggattggg aagacaatag caggcatgct ggggatgcgg tgggctctat    6180
ggcttctgag gcggaaagaa ccagctgggg ctctaggggg tatccccacg cgccctgtag    6240
cggcgcatta agcgcggcgg gtgtggtggt tacgcgcagc gtgaccgcta cacttgccag    6300
```

| | | | | |
|---|---|---|---|---|
| cgccctagcg | cccgctcctt | tcgctttctt | cccttcctttt | ctcgccacgt tcgccggctt | 6360 |
| tccccgtcaa | gctctaaatc | ggggggctccc | tttagggttc | cgatttagtg ctttacggca | 6420 |
| cctcgacccc | aaaaaacttg | attagggtga | tggttcacgt | agtgggccat cgccctgata | 6480 |
| gacggttttt | cgcccttttga | cgttggagtc | cacgttcttt | aatagtggac tcttgttcca | 6540 |
| aactggaaca | acactcaacc | ctatctcggt | ctattcttttt | gatttataag ggattttgcc | 6600 |
| gatttcggcc | tattggttaa | aaaatgagct | gatttaacaa | aaatttaacg cgaattaatt | 6660 |
| ctgtggaatg | tgtgtcagtt | agggtgtgga | agtccccag | gctccccagc aggcagaagt | 6720 |
| atgcaaagca | tgcatctcaa | ttagtcagca | accaggtgtg | gaaagtcccc aggctcccca | 6780 |
| gcaggcagaa | gtatgcaaag | catgcatctc | aattagtcag | caaccatagt cccgcccta | 6840 |
| actccgccca | tcccgcccct | aactccgccc | agttccgccc | attctccgcc ccatggctga | 6900 |
| ctaattttttt | ttatttatgc | agaggccgag | gccgcctctg | cctctgagct attccagaag | 6960 |
| tagtgaggag | gctttttttgg | aggcctaggc | ttttgcaaaa | agctcccggg agcttgtata | 7020 |
| tccattttcg | gatctgatca | gcacgtgttg | acaattaatc | atcggcatag tatatcggca | 7080 |
| tagtataata | cgacaaggtg | aggaactaaa | ccatggccaa | gttgaccagt gccgttccgg | 7140 |
| tgctcaccgc | gcgcgacgtc | gccggagcgg | tcgagttctg | gaccgaccgg ctcgggttct | 7200 |
| cccgggactt | cgtggaggac | gacttcgccg | gtgtggtccg | ggacgacgtg accctgttca | 7260 |
| tcagcgcggt | ccaggaccag | gtggtgccgg | acaacaccct | ggcctgggtg tgggtgcgcg | 7320 |
| gcctggacga | gctgtacgcc | gagtggtcgg | aggtcgtgtc | cacgaacttc cgggacgcct | 7380 |
| ccgggccggc | catgaccgag | atcggcgagc | agccgtgggg | gcgggagttc gccctgcgcg | 7440 |
| acccggccgg | caactgcgtg | cacttcgtgg | ccgaggagca | ggactgacac gtgctacgag | 7500 |
| atttcgattc | caccgccgcc | ttctatgaaa | ggttgggctt | cggaatcgtt ttccgggacg | 7560 |
| ccggctggat | gatcctccag | cgcggggatc | tcatgctgga | gttcttcgcc cacccccaact | 7620 |
| tgtttattgc | agcttataat | ggttacaaat | aaagcaatag | catcacaaat ttcacaaata | 7680 |
| aagcatttttt | ttcactgcat | tctagttgtg | gtttgtccaa | actcatcaat gtatcttatc | 7740 |
| atgtctgtat | accgtcgacc | tctagctaga | gcttggcgta | atcatggtca tagctgtttc | 7800 |
| ctgtgtgaaa | ttgttatccg | ctcacaattc | cacacaacat | acgagccgga agcataaagt | 7860 |
| gtaaagcctg | gggtgcctaa | tgagtgagct | aactcacatt | aattgcgttg cgctcactgc | 7920 |
| ccgctttcca | gtcgggaaac | ctgtcgtgcc | agctgcatta | atgaatcggc caacgcgcgg | 7980 |
| ggagaggcgg | tttgcgtatt | gggcgctctt | ccgcttcctc | gctcactgac tcgctgcgct | 8040 |
| cggtcgttcg | gctgcggcga | gcggtatcag | ctcactcaaa | ggcggtaata cggttatcca | 8100 |
| cagaatcagg | ggataacgca | ggaaagaaca | tgtgagcaaa | aggccagcaa aaggccagga | 8160 |
| accgtaaaaa | ggccgcgttg | ctggcgtttt | tccataggct | ccgcccccct gacgagcatc | 8220 |
| acaaaaatcg | acgctcaagt | cagaggtggc | gaaacccgac | aggactataa agataccagg | 8280 |
| cgtttccccc | tggaagctcc | ctcgtgcgct | ctcctgttcc | gaccctgccg cttaccggat | 8340 |
| acctgtccgc | ctttctccct | tcgggaagcg | tggcgctttc | tcatagctca cgctgtaggt | 8400 |
| atctcagttc | ggtgtaggtc | gttcgctcca | agctgggctg | tgtgcacgaa ccccccgttc | 8460 |
| agcccgaccg | ctgcgcctta | tccggtaact | atcgtcttga | gtccaacccg gtaagacacg | 8520 |
| acttatcgcc | actggcagca | gccactggta | acaggattag | cagagcgagg tatgtaggcg | 8580 |
| gtgctacaga | gttcttgaag | tggtggccta | actacggcta | cactagaaga acagtatttg | 8640 |
| gtatctgcgc | tctgctgaag | ccagttacct | tcggaaaaag | agttggtagc tcttgatccg | 8700 |

```
gcaaacaaac caccgctggt agcggtggtt tttttgtttg caagcagcag attacgcgca      8760
gaaaaaaagg atctcaagaa gatcctttga tctttctac ggggtctgac gctcagtgga       8820
acgaaaactc acgttaaggg attttggtca tgagattatc aaaaaggatc ttcacctaga      8880
tccttttaaa ttaaaaatga agttttaaat caatctaaag tatatatgag taaacttggt      8940
ctgacagtta ccaatgctta atcagtgagg cacctatctc agcgatctgt ctatttcgtt      9000
catccatagt tgcctgactc cccgtcgtgt agataactac gatacgggag ggcttaccat      9060
ctggccccag tgctgcaatg ataccgcgag acccacgctc accggctcca gatttatcag      9120
caataaacca gccagccgga agggccgagc gcagaagtgg tcctgcaact ttatccgcct      9180
ccatccagtc tattaattgt tgccgggaag ctagagtaag tagttcgcca gttaatagtt      9240
tgcgcaacgt tgttgccatt gctacaggca tcgtggtgtc acgctcgtcg tttggtatgg      9300
cttcattcag ctccggttcc caacgatcaa ggcgagttac atgatccccc atgttgtgca      9360
aaaaagcggt tagctccttc ggtcctccga tcgttgtcag aagtaagttg gccgcagtgt      9420
tatcactcat ggttatggca gcactgcata attctcttac tgtcatgcca tccgtaagat      9480
gcttttctgt gactggtgag tactcaacca agtcattctg agaatagtgt atgcggcgac      9540
cgagttgctc ttgcccggcg tcaatacggg ataataccgc gccacatagc agaactttaa      9600
aagtgctcat cattggaaaa cgttcttcgg ggcgaaaact ctcaaggatc ttaccgctgt      9660
tgagatccag ttcgatgtaa cccactcgtg cacccaactg atcttcagca tcttttactt      9720
tcaccagcgt ttctgggtga gcaaaaacag gaaggcaaaa tgccgcaaaa aagggaataa      9780
gggcgacacg gaaatgttga atactcatac tcttcctttt tcaatattat tgaagcattt      9840
atcagggtta ttgtctcatg agcggataca tatttgaatg tatttagaaa aataaacaaa      9900 tagggggttcc gcgcacattt ccccgaaaag tgccacctga c                        9941

<210> SEQ ID NO 4
<211> LENGTH: 334
<212> TYPE: DNA
<213> ORGANISM: Homo sapiens

<400> SEQUENCE: 4
ccccagtgga agacgcgcca ggcaaaacgc accacgtgac ggagcgtgac cgcgcgccga       60
gcgcgcgcca aggtcgggca ggaagagggc ctatttccca tgattccttc atatttgcat      120
atacgataca aggctgttag agagataatt agaattaatt tgactgtaaa cacaaagata      180
ttagtacaaa atacgtgacg tagaaagtaa taatttcttg ggtagtttgc agttttaaaa      240
ttatgtttta aaatggacta tcatatgctt accgtaactt gaaagtattt cgatttcttg      300
gctttatata tcttgtggaa aggacgaaac accg                                  334

<210> SEQ ID NO 5
<211> LENGTH: 246
<212> TYPE: DNA
<213> ORGANISM: Homo sapiens

<400> SEQUENCE: 5
tctagaccat ggaattcgaa cgctgacgtc atcaacccgc tccaaggaat cgcgggccca       60
gtgtcactag gcgggaacac ccagcgcgcg tgcgccctgg caggaagatg gctgtgaggg      120
acaggggagt ggcgccctgc aatatttgca tgtcgctatg tgttctggga aatcaccata      180
aacgtgaaat gtctttggat ttgggaatct tataagttct gtatgagacc acggatccaa      240
```

-continued aagctt 246

<210> SEQ ID NO 6
<211> LENGTH: 355
<212> TYPE: DNA
<213> ORGANISM: Artificial Sequence
<220> FEATURE:
<223> OTHER INFORMATION: This represents a mutant human sequence
having an introduced bacterial tetO1 binding site.

<400> SEQUENCE: 6

```
gggaattccc ccagtggaaa gacgcgcagg caaaacgcac cacgtgacgg agcgtgaccg      60
cgcgccgagc ccaaggtcgg gcaggaagag ggcctatttc ccatgattcc ttcatatttg     120
catatacgat acaaggctgt tagagagata attagaatta atttgactgt aaacacaaag     180
atattagtac aaaatacgtg acgtagaaag taataatttc ttgggtagtt tgcagttttta    240
aaattatgtt ttaaaatgga ctatcatatg cttaccgtaa cttgaaagta ctctatcatt     300
gatagagtta tatatcttgt ggaaaggacg aaacaccgtg gtcttcaagc ttccg          355
```

<210> SEQ ID NO 7
<211> LENGTH: 634
<212> TYPE: DNA
<213> ORGANISM: E. coli

<400> SEQUENCE: 7

```
gctagccacc atgtccagat tagataaaag taaagtgatt aacagcgcat tagagctgct      60
taatgaggtc ggaatcgaag gtttaacaac ccgtaaactc gcccagaagc taggtgtaga    120
gcagcctaca ttgtattggc atgtaaaaaa taagcgggct ttgctcgacg ccttagccat    180
tgagatgtta gataggcacc atactcactt ttgcccttta gaaggggaaa gctggcaaga    240
tttttttacgt aataacgcta aaagttttag atgtgcttta ctaagtcatc gcgatggagc    300
aaaagtacat ttaggtacac ggcctacaga aaaacagtat gaaactctcg aaaatcaatt    360
agcctttta tgccaacaag gttttttcact agagaatgca ttatatgcac tcagcgctgt    420
ggggcatttt actttaggtt gcgtattgga agatcaagag catcaagtcg ctaaagaaga    480
aagggaaaca cctactactg atagtatgcc gccattatta cgacaagcta tcgaattatt    540
tgatcaccaa ggtgcagagc cagccttctt attcggcctt gaattgatca tatgcggatt    600
agaaaaacaa cttaaatgtg aaagtgggtc ttaa                                 634
```

<210> SEQ ID NO 8
<211> LENGTH: 60
<212> TYPE: DNA
<213> ORGANISM: Artificial Sequence
<220> FEATURE:
<223> OTHER INFORMATION: This represents an anti-human specific siRNA
cassette comprising human sequence and synthetic
linker, loop and terminator sequences.

<400> SEQUENCE: 8

```
gatccccgaa gatacacagc agttgtttca agagaacaac tgctgtgtat cttcttttc       60
```

<210> SEQ ID NO 9
<211> LENGTH: 60
<212> TYPE: DNA
<213> ORGANISM: Artificial Sequence
<220> FEATURE:

<223> OTHER INFORMATION: This represents an anti-human specific siRNA
cassette comprising human sequence and synthetic
linker, loop and terminator sequences.

<400> SEQUENCE: 9

```
gatccccgta ccgtgtctgc aatgtgttca agagacacat tgcagacacg gtacttttc      60
```

<210> SEQ ID NO 10
<211> LENGTH: 246
<212> TYPE: DNA
<213> ORGANISM: Homo sapiens

<400> SEQUENCE: 10

```
tctagaccat ggaattcgaa cgctgacgtc atcaacccgc tccaaggaat cgcgggccca      60
gtgtcactag gcgggaacac ccagcgcgcg tgcgccctgg caggaagatg gctgtgaggg     120
acagggagt ggcgccctgc aatatttgca tgtcgctatg tgttctggga aatcaccata      180
aacgtgaaat gtctttggat ttgggaatct tataagttct gtatgagacc acggatccaa     240
aagctt                                                                246
```

<210> SEQ ID NO 11
<211> LENGTH: 348
<212> TYPE: DNA
<213> ORGANISM: Homo sapiens

<400> SEQUENCE: 11

```
atggcaggaa gaagcggaga cagcgacgaa gagctcatca gaacagtcag actcatcaag      60
cttctctatc aaagcccacc tcccaatccc gaggggaccc gacaggcccg aaggaataga     120
agaagaaggt ggagagagag acagagacag atccattcga ttagtgaacg gatccttagc     180
acttatctgg gacgatctgc ggagcctgtg cctcttcagc taccaccgct tgagagactt     240
actcttgatt gtaacgagga ttgtggaact tctgggacgc aggggtggg aagccctcaa      300
atattggtgg aatctcctac agtattggag tcaggaacta aagaatag                  348
```

<210> SEQ ID NO 12
<211> LENGTH: 348
<212> TYPE: DNA
<213> ORGANISM: Artificial Sequence
<220> FEATURE:
<223> OTHER INFORMATION: This sequence represents mutant human sequence.

<400> SEQUENCE: 12

```
atggcaggaa gaagcggaga cagcgacgaa gagctcatca gaacagtcag actcatcaag      60
cttctctatc aaagcccacc tcccaatccc gaggggaccc gacaggcccg aaggaataga     120
agaagaaggt ggcgtgagag acagagacag atccattcga ttagtgaacg gatccttagc     180
acttatctgg gacgatctgc ggagcctgtg cctcttcagc taccaccgct tgagagactt     240
actcttgatt gtaacgagga ttgtggaact tctgggacgc aggggtggg aagccctcaa      300
atattggtgg aatctcctac agtattggag tcaggaacta aagaatag                  348
```

METHOD FOR EXPRESSION OF SMALL ANTIVIRAL RNA MOLECULES WITHIN A CELL

REFERENCE TO RELATED APPLICATIONS

The present application claims priority as a continuation-in-part of U.S. application Ser. No. 10/243,553, filed Sep. 13, 2002, which claims priority to U.S. Provisional Application No. 60/322,031, filed Sep. 13, 2001, U.S. Provisional Application No. 60/347,782, filed Jan. 9, 2002, U.S. Provisional Application No. 60/389,592, filed Jun. 18, 2002, and U.S. Provisional Application No. 60/406,436, filed Aug. 27, 2002.

GOVERNMENT SUPPORT

This invention was made with government support under Grant Number GM39458 awarded by the National Institutes of Health. The United States Government has certain rights in the invention.

BACKGROUND OF THE INVENTION

1. Field of the Invention

The present invention relates generally to methods for altering gene expression in a cell or animal using viral constructs engineered to deliver an RNA molecule, and more specifically to deliver double-stranded RNA molecules that can be used to down-regulate or modulate gene expression. Particular aspects of the invention relate to down-regulating a pathogenic virus gene or a gene necessary for a pathogenic virus life cycle through delivery of a viral construct engineered to express an RNA molecule.

2. Description of the Related Art

RNA interference (RNAi) or silencing is a recently discovered phenomenon (A. Fire et al., Nature 391, 806 (1998); C. E. Rocheleau et al. Cell 90, 707 (1997)). Small interfering RNAs ("siRNAs") are double-stranded RNA molecules that inhibit the expression of a gene with which they share homology. siRNAs have been used as a tool to down regulate the expression of specific genes in a variety of cultured cells as well as in invertebrate animals. A number of such approaches have been reviewed recently (P. D. Zamore Science 296, 1265 (2002)); however, such approaches have limitations. For example, no technique prior to the invention described herein allows for the generation of transgenic mammals having a specific gene down regulated through RNA interference. Similarly, there is a need for more robust methods for the introduction of small RNA molecules with regulatory function. The invention provided herein addresses these and other limitations in the field of RNA mediated gene regulation. Likewise, there is a need for improved methods and compositions for the treatment of viruses and diseases associated with viral infection.

SUMMARY OF THE INVENTION

The invention relates generally to methods to express within a cell an RNA molecule or molecules. These methods can be used with a wide variety of cell types. RNA molecules can be expressed within a cell for a variety of purposes. For example, RNA molecules can serve as markers within a cell, can be antisense oligonucleotides or ribozymes for regulating gene expression, and can serve to down regulate genes through RNA interference.

In one aspect, the methods of the invention relate to the treatment or prevention of infection through the expression of one or more RNA molecules that inhibit one or more aspects of the life cycle of a pathogen through RNA interference with a target nucleic acid, such as a viral genome, a viral transcript or a host cell gene that is necessary for viral replication.

According to another aspect of the invention, a method of expressing an RNA molecule is provided which includes transfecting a packaging cell line with a retroviral construct and recovering recombinant retrovirus from the packaging cell line. A host cell is then infected with the recombinant retrovirus.

The recombinant retrovirus construct preferably has a first RNA polymerase III promoter region, at least one RNA coding region, and at least one termination sequence. The RNA coding region preferably comprises a sequence that is at least about 90% identical to a target sequence within the target-nucleic acid. Preferably the target nucleic is necessary for the life cycle of a pathogen, for example, part of a pathogenic virus RNA genome or genome transcript, or part of a target cell gene involved in the life cycle of a pathogenic virus.

In one embodiment, the methods of the invention are used to disrupt the life cycle of a pathogen. In a particular embodiment the methods are used to disrupt the life cycle of a virus having an RNA genome, for example a retrovirus, by targeting the RNA genome directly. In another embodiment a viral genome transcript is targeted, including transcripts of individual viral genes. The methods also can be used to down regulate a gene in a host cell, where the gene is involved in the viral life cycle, for example, a receptor or co-receptor necessary for viral entry into the host cell.

In one aspect of the invention, the RNA coding region encodes an siRNA, preferably a self-complementary "hairpin" RNA molecule having a sense region, an antisense region and a loop region. The loop region is generally between about 2 and about 15 nucleotides in length, and in a more preferred embodiment is about 6 to about 9 nucleotides in length. The double-stranded region of the hairpin molecule comprises a nucleotide sequence that is homologous to the target sequence. The sequence in the hairpin molecule is preferably at least about 90% identical to a target sequence, more preferably at least about 95% identical, even more preferably at least about 99% identical.

In another embodiment, the RNA coding region encodes a first RNA molecule, and the retroviral construct has a second RNA polymerase III promoter and a second RNA coding region operably linked to the second RNA polymerase III promoter. In such an embodiment, the second RNA coding region encodes an RNA molecule substantially complementary to the first RNA molecule. Upon expression of the first and second RNA coding regions, a double-stranded complex is formed within a cell.

In yet another embodiment, the retroviral construct can have a second RNA polymerase III promoter region operably linked to the RNA coding region, such that expression of the RNA coding region from the first RNA polymerase III promoter results in the synthesis of a first RNA molecule and expression of the RNA coding region from the second RNA polymerase III promoter results in synthesis of a second RNA molecule substantially complementary to the first RNA molecule. In one such embodiment, the RNA polymerase III promoters are separated from the RNA coding region by termination sequences.

In one embodiment of the invention, the target cell is an embryonic cell. An embryonic cell as used herein includes a single cell embryo, and embryo cells within an early-stage embryo. In another embodiment of the invention, the target cell is an embryogenic stem cell. When the target cell is an embryonic cell, the embryonic cell can be infected by injecting the recombinant retrovirus between the zona pellucida and the cell membrane of a mammalian embryonic cell. In another embodiment, the embryonic cell can be infected by removing the zona pellucida and incubating the cell in solution containing the recombinant retrovirus. In such an embodiment, the zona pellucida can be removed by enzymatic digestion. When the target cell is an embryonic cell or an embryogenic stem cell, the methods of the invention also include implanting the embryonic cell in a pseudopregnant female to generate a transgenic animal. In such a fashion, a transgenic animal can be generated that is resistant to a particular pathogen, such as a virus.

The methods of the invention can also be used with a variety of primary, ex vivo normal or diseased cells or cells adapted in various tissue culture conditions. The cells are preferably obtained from human, mouse or other vertebrates. The cells may include, without limitation, hematopoietic stem or precursor cells, central nerve system cells, cells with regenerative capacities for a variety of other tissues and organs, dendritic cells and other developing and mature myeloid and lymphoid cells, and cancer cells derived from different cell lineages.

In another aspect the invention provides retroviral constructs for the expression of an RNA molecule or molecules within a cell. The constructs preferably comprise an RNA polymerase III (pol III) promoter. In one embodiment the retroviral constructs have an RNA coding region operably linked to the RNA polymerase III promoter. The RNA coding region can be immediately followed by a pol III terminator sequence, which directs termination of RNA synthesis by pol III. The pol III terminator sequences generally have 4 or more consecutive thymidine ("T") residues. In a preferred embodiment, a cluster of 5 consecutive Ts is used as the terminator by which pol III. transcription is stopped at the second or third T of the DNA template, and thus only 2 to 3 uridine ("U") residues are added to the 3' end of the coding sequence. A variety of pol III promoters can be used with the invention, including for example, the promoter fragments derived from H1 RNA genes or U6 snRNA genes of human or mouse origin or from any other species. In addition, pol III promoters can be modified/ engineered to incorporate other desirable properties such as the ability to be induced by small chemical molecules, either ubiquitously or in a tissue-specific manner. For example, in one embodiment the promoter may be activated by tetracycline. In another embodiment the promoter may be activated by IPTG (lacI system).

The retroviral construct can be based on a number of retroviral vectors. In a preferred embodiment, the retroviral construct has the R and U5 sequences from a 5' lentiviral long terminal repeat (LTR) and a self-inactivating lentiviral 3' LTR. In another embodiment, the :retroviral vector is derived from the murine stem cell virus (MSCV). In yet another embodiment, the retroviral construct is a hybrid of a lentiviral and a MSCV construct.

In a further embodiment, the RNA coding region encodes a self-complementary RNA molecule having a sense region, an antisense region and a loop region. Such an RNA molecule, when expressed, preferably forms a "hairpin" structure. A loop region is generally between about 2 to 15 nucleotides in length. In a preferred embodiment, the loop region is from 6 to 9 nucleotides in length. In one such embodiment of the invention, the sense region and the antisense region are between about 15 and about 30 nucleotides in length. In one embodiment, the RNA coding region of this embodiment of invention is operably linked downstream to an RNA polymerase III promoter in such that the RNA coding sequence can be precisely expressed without any extra non-coding nucleotides present at 5' end (ie., the expressed sequence is identical to the target sequence at the 5' end). The synthesis of the RNA coding region is ended at the terminator site. In one preferred embodiment the terminator has five consecutive T residues.

In another aspect of the invention, the retroviral vector can contain multiple RNA coding regions. In one such embodiment, the RNA coding region encodes a first RNA molecule, and the retroviral construct has a second RNA polymerase III promoter and a second RNA coding region operably linked to the second RNA polymerase III promoter. In this embodiment, the second RNA molecule can be substantially complementary to the first RNA molecule, such that the first and the second RNA molecules can form a double-stranded structure when expressed. The double stranded region of the RNA complex is at least about 90% identical to a target region of either a viral genome, a viral genome transcript or a target cell RNA encoding a protein necessary for the pathogenic virus life cycle. The methods of invention also include multiple RNA coding regions that encode hairpin-like self-complementary RNA molecules or other non-hairpin molecules.

In yet another embodiment of the invention, the retroviral construct has a second RNA polymerase III promoter operably linked to the same RNA coding region in the opposite direction, such that expression of the RNA coding region from the first RNA polymerase III promoter results in a synthesis of a first RNA molecule as the sense strand and expression of the RNA coding region from the second RNA polymerase III promoter results in synthesis of a second RNA molecule as antisense strand with substantial complementarity to the first RNA molecule. In such an embodiment, both RNA molecules can contain a 3' overhang of residues encoded by the termination sequence. In one embodiment, both RNA polymerase III promoters are separated from the RNA coding region by termination sequences. Preferably the termination sequences comprise five consecutive T residues.

According to another aspect of the invention, the 5' LTR sequences can be derived from HIV. The retroviral construct can also have a woodchuck hepatitis virus enhancer element sequence and/or a tRNA amber suppressor sequence.

In one embodiment of the invention, the self-inactivating 3' LTR can be a U3 element with a deletion of its enhancer sequence. In yet another embodiment, the self-inactivating 3' LTR is a modified HIV 3' LTR.

The recombinant retroviral construct can be pseudotyped, for example with the vesicular stomatitits virus envelope glycoprotein.

According to another aspect of the invention, the viral construct also can encode a gene of interest. The gene of interest can be linked to a Polymerase II promoter. A variety of Polymerase II promoters can be used with the invention, including for example, the CMV promoter. The RNA Polymerase II promoter that is chosen can be a ubiquitous promoter, capable of driving expression in most tissues, for example, the human Ubiquitin-C promoter, CMV β-actin promoter and PGK promoter. The RNA Polymerase II promoter also can be a tissue-specific promoter. Such a construct also can contain, for example, an enhancer sequence operably linked with the Polymerase II promoter.

In one embodiment, the gene of interest is a marker or reporter gene that can be used to verify that the vector was successfully transfected or transduced and its sequences expressed. In one such embodiment, the gene of interest is a fluorescent reporter gene, for example, the Green Fluorescent Protein. In yet another embodiment, the gene of interest is a drug resistant gene which can be used to select the cells that are successfully transduced. For example, the drug resistant gene can be the zeocin resistant gene (zeo). The gene of interest also can be a hybrid of a drug resistant gene and a fluorescent reporter gene, such as a zeo/gfp fusion. In another aspect of the invention, the gene of interest encodes a protein factor that can regulate the transcription activity of inducible pol III promoters. In one of such embodiment, the gene of interest is tetR (repressor for tet operon) which regulates tetracycline responsive pol III promoters.

It is another aspect of the invention to provide methods for expressing an, RNA molecule or molecules within a cell. In one embodiment a packaging cell line is transfected with a retroviral construct of the invention, recombinant retroviral particles are recovered from the packaging cell line; and a target cell is infected with the recombinant retrovirus particles. According to such methods, the retroviral construct has the R and U5 sequences from a 5' lentiviral long terminal repeat (LTR), a self-inactivating lentiviral 3' LTR, a first RNA polymerase III promoter region and at least one RNA coding region. The retroviral construct also can have a termination sequence operably linked to the RNA coding region.

In a further aspect a method of treating a patient suffering from HIV infection is provided. In one embodiment, a CD34-positive target cell is isolated from the patient. The target cell is then infected with a recombinant retrovirus recovered from a packaging cell line transfected with a retroviral construct of the invention. Preferably, the recombinant retroviral construct comprises a first RNA polymerase III promoter region, at least one RNA coding region, and at least one termination sequence. In one embodiment the RNA coding region comprises a sequence that is at least about 90% identical to a target region of the HIV genome, an HIV genome transcript or a cellular gene that is involved in the HIV life cycle. The target region is preferably from about 18 to about 23 nucleotides in length.

In one embodiment the RNA coding region encodes a hairpin RNA molecule.

In a preferred embodiment, the RNA coding region is at least about 90% identical to a target region of the CCR5 gene or the CXCR4 gene.

In a still further aspect, a method of producing high titer siRNA encoding lentivirus is provided, particularly where the siRNA activity may interfere with the virus life cycle or a cellular gene.

In one embodiment a method of producing recombinant retrovirus comprises cotransfecting a packaging cell line with a retroviral construct comprising a first RNA coding region that is at least about 90% identical to a target region of a first gene and a first vector comprising a second RNA coding region that is at least about 90% identical to a target region of a second gene, wherein expression of the second gene mediates RNA interference. The first and second RNA coding regions preferably encode RNA molecules having a sense region, an antisense region and a loop region, wherein the sense region is substantially complementary to the antisense region.

The first RNA coding region is preferably at least about 90% identical to a gene selected from the group consisting of genes within the genome of a pathogenic virus, cellular genes that are involved in the lifecycle of a pathogenic virus and genes that mediate a disease or disorder. In a particular embodiment the first RNA coding region is at least about 90% identical to a gene from the HIV virus, such as gag, pol or rev.

The second gene is preferably selected from the group of genes that encode Dicer-1, Dicer-2, FMR1, eIF2C2, eIF2C1 (GERp95)/hAgo1, eIF2C2/hAgo2, hAgo 3, hAgo4, hAgo5, Hiwi1/Miwi1, Hiwi2/ Miwi2, Hili/Mili, Gemin3, P678 helicase, Gemin2, Gemin4, P115/ slicer and VIG. More preferably the second gene encodes Dicer-1 or eIF2C2.

In one embodiment the second RNA coding region comprises a sequence that is at least about 90% identical to a portion of the gene encoding Dicer-1 or a portion of the gene encoding eIF2C2. In a particular embodiment the second RNA coding region comprises the sequence of SEQ ID NO: 8, while in another embodiment the second RNA coding region comprises the sequence of SEQ ID NO: 9.

The packaging cell line may additionally be cotransfected with a second vector comprising a third RNA coding region that is at least about 90% identical to a target region of a third gene, wherein expression of the third gene mediates RNA interference. The third gene is preferably selected from the group consisting of the genes encoding Dicer-1, Dicer-2, FMR1, eIF2C2, eIF2C1 (GERp95)/hAgo1, eIF2C2/ hAgo2, hAgo3, hAgo4, hAgo5, Hiwi1/Miwi1, Hiwi2/ Miwi2, Hili/ Mili, Gemin3, P678 helicase, Gemin2, Gemin4, P115/ slicer and VIG. More preferably the third gene encodes Dicer-1 or eIF2C2.

In a further embodiment a method of producing recombinant retrovirus is provided comprising transfecting a packaging cell with a retroviral construct comprising a first RNA coding region that is at least about 90% identical to a portion of a target gene and inhibiting RNA interference in the packaging cell.

RNA interference is preferably inhibited by expressing siRNA in the packaging cell that is at least about 90% identical to a gene that mediates RNA interference. The siRNA may be transiently expressed in the packaging cell or stably expressed.

In another embodiment a method of producing siRNA encoding lentivirus is provided where the siRNA activity may interfere with an aspect of the virus lifecycle. A packaging cell is transfected with a vector encoding the lentivirus and siRNA activity is inhibited in the packaging cell.

DETAILED DESCRIPTION OF THE PREFERRED EMBODIMENT

Figure 1A:
FIG. 1A shows a schematic diagram of a retroviral vector carrying an expression cassette for RNA expression, termed "RNA cassette" and a "Marker Gene" or gene of interest. The RNA expression cassette can be embedded at any permissible sites of the retroviral construct either as single copy or multiple tandem copies. In addition, although not indicated in the figure, more than one RNA expression cassette may be present in the retroviral construct.

The inventors have identified a method for introducing a transgene of interest into a cell or animal. This technique is described in copending U.S. provisional patent application 60/322,031 filed on Sep. 9, 2001 and copending U.S. provisional patent application 60/347,782 filed on Jan. 9, 2002, the entire contents of which are incorporated herein by reference.

Unless defined otherwise, all technical and scientific terms used herein have the same meaning as commonly understood by one of ordinary skill in the art to which this invention belongs. Any methods, devices and materials similar or equivalent to those described herein can be used in the practice of this invention.

By "transgene" is meant any nucleotide sequence, particularly a DNA sequence, that is integrated into one or more chromosomes of a host cell by human intervention, such as by the methods of the present invention. In one embodiment, a transgene is an "RNA coding region." In another embodiment the transgene comprises a "gene of interest." In other embodiments the transgene can be a nucleotide sequence, preferably a DNA sequence, that is used to mark the chromosome where it has integrated. In this situation, the transgene does not have to comprise a gene that encodes a protein that can be expressed.

A "gene of interest" is a nucleic acid sequence that encodes a protein or other molecule that is desirable for integration in a host cell. In one embodiment, the gene of interest encodes a protein or other molecule the expression of which is desired in the host cell. In this embodiment, the gene of interest is generally operatively linked to other sequences that are useful for obtaining the desired expression of the gene of interest, such as transcriptional regulatory sequences.

A "functional relationship" and "operably linked" mean, without limitation, that the gene is in the correct location and orientation with respect to the promoter and/or enhancer that expression of the gene will be affected when the promoter and/or enhancer is contacted with the appropriate molecules.

An "RNA coding region" is a nucleic acid that can serve as a template for the synthesis of an RNA molecule, such as an siRNA. Preferably, the RNA coding region is a DNA sequence.

A "small interfering RNA" or "siRNA" is a double-stranded RNA molecule that is capable of inhibiting the expression of a gene with which it shares homology. The region of the gene or other nucleotide sequence over which there is homology is known as the "target region." In one embodiment the siRNA may be a "hairpin" or stem-loop RNA molecule, comprising a sense region, a loop region and an antisense region complementary to the sense region. In other embodiments the siRNA comprises two distinct RNA molecules that are non-covalently associated to form a duplex.

The term "animal" is used in its broadest sense and refers to all animals including mammals, birds, fish, reptiles and amphibians.

The term "mammal" refers to all members of the class Mammalia and includes any animal classified as a mammal, including humans, domestic and farm animals, and zoo, sports or pet animals, such as mouse, rabbit, pig, sheep, goat, cattle and higher primates.

"Target cell" or "host cell" means a cell that is to be transformed using the methods and compositions of the invention.

The term "pathogenic virus" is used herein to indicate a virus capable of infecting an animal.

"Retroviruses" are viruses having an RNA genome.

"Lentivirus" refers to a genus of retroviruses that are capable of infecting dividing and non-dividing cells. Several examples of lentiviruses include HIV (human immunodeficiency virus: including HIV type 1, and HIV type 2), the etiologic agent of the human acquired immunodeficiency syndrome (AIDS); visna-maedi, which causes encephalitis (visna) or pneumonia (maedi) in sheep, the caprine arthritis-encephalitis virus, which causes immune deficiency, arthritis, and encephalopathy in goats; equine infectious anemia virus, which causes autoimmune hemolytic anemia, and encephalopathy in horses; feline immunodeficiency virus (FIV), which causes immune deficiency in cats; bovine immune deficiency virus (BIV), which causes lymphadenopathy, lymphocytosis, and possibly central nervous system infection in cattle; and simian immunodeficiency virus (SIV), which cause immune deficiency and encephalopathy in sub-human primates.

A "hybrid virus" as used herein refers to a virus having components from one or more other viral vectors, including element from non-retroviral vectors, for example, adenoviral-retroviral hybrids. As used herein hybrid vectors having a retroviral component are to be considered within the scope of the retroviruses.

A lentiviral genome is generally organized into a 5' long terminal repeat (LTR), the gag gene, the pol gene, the env gene, the accessory genes (nef, vif, vpr, vpu) and a 3' LTR. The viral LTR is divided into three regions called U3, R and U5. The U3 region contains the enhancer and promoter elements. The U5 region contains the polyadenylation signals. The R (repeat) region separates the U3 and U5 regions and transcribed sequences of the R region appear at both the 5' and 3' ends of the viral RNA. See, for example, "RNA Viruses: A Practical Approach" (Alan J. Cann, Ed., Oxford University Press, (2000)), O Narayan and Clements J. Gen. Virology 70:1617–1639 (1989), Fields et al. Fundamental Virology Raven Press. (1990), Miyoshi H, Blomer U, Takahashi M, Gage F H, Verma I M. *J Virol.* 72(10):8150–7 (1998), and U.S. Pat. No. 6,013,516.

Lentiviral vectors are known in the art, including several that have been used to transfect hematopoietic stem cells. Such vectors can be found, for example, in the following publications, which are incorporated herein by reference: Evans J T et al. *Hum Gene Ther* 1999;10:1479–1489; Case S S, Price M A, Jordan C T et al. *Proc Natl Acad Sci USA* 1999;96:2988–2993; Uchida N, Sutton R E, Friera A M et al. Proc Natl Acad Sci USA 1998;95:11939–11944; Miyoshi H, Smith K A, Mosier D E et al. *Science* 1999;283:682–686; Sutton R E, Wu H T, Rigg R et al. Human immunodeficiency virus type 1 vectors efficiently transduce human hematopoietic stem cells. *J Virol* 1998;72:5781–5788.

"Virion," "viral particle" and "retroviral particle" are used herein to refer to a single virus comprising an RNA genome, pol gene derived proteins, gag gene derived proteins and a lipid bilayer displaying an envelope (glyco)protein. The RNA genome is usually a recombinant RNA genome and thus may contain an RNA sequence that is exogenous to the native viral genome. The RNA genome may also comprise a defective endogenous viral sequence.

A "pseudotyped" retrovirus is a retroviral particle having an envelope protein that is from a virus other than the virus from which the RNA genome is derived. The envelope protein may be from a different retrovirus or from a non-retroviral virus. A preferred envelope protein is the vesicular stomatitus virus G (VSV G) protein. However, to eliminate the possibility of human infection, viruses can alternatively be pseudotyped with ecotropic envelope protein that limit infection to a specific species, such as mice or birds. For example, in one embodiment, a mutant ecotropic envelope protein is used, such as the ecotropic envelope protein 4.17 (Powell et al. Nature Biotechnology 18(12):1279–1282 (2000)).

The term "provirus" is used to refer to a duplex DNA sequence present in a eukaryotic chromosome that corresponds to the genome of an RNA retrovirus. The provirus may be transmitted from one cell generation to the next without causing lysis or destruction of the host cell.

A "self-inactivating 3' LTR" is a 3' long terminal repeat (LTR) that contains a mutation, substitution or deletion that prevents the LTR sequences from driving expression of a downstream gene. A copy of the U3 region from the 3' LTR acts as a template for the generation of both LTR's in the integrated provirus. Thus, when the 3' LTR with an inactivating deletion or mutation integrates as the 5' LTR of the provirus, no transcription from the 5' LTR is possible. This eliminates competition between the viral enhancer/promoter and any internal enhancer/promoter. Self-inactivating 3' LTRs are described, for example, in Zufferey et al. *J Virol.* 72:9873–9880 (1998), Miyoshi et al. *J Virol.* 72:8150–8157 and Iwakuma et al. *Virology* 261:120–132 (1999).

The term "RNA interference or silencing" is broadly defined to include all posttranscriptional and transcriptional mechanisms of RNA mediated inhibition of gene expression, such as those described in P. D. Zamore *Science* 296, 1265 (2002).

"Substantial complementarity" and "substantially complementary" as used herein indicate that two nucleic acids are at least 80% complementary, more preferably at least 90% complementary and most preferably at least 95% complementary over a region of more than about 15 nucleotides and more preferably more than about 19 nucleotides.

In one aspect of the invention, a recombinant retrovirus is used to deliver an RNA coding region of interest to a cell, preferably a mammalian cell. The cell may be a primary cell or a cultured cell. In one embodiment the cell is an oocyte or an embryonic cell, more preferably a one-cell embryo. In another embodiment the cell is a hematopoietic stem cell. The RNA coding region and any associated genetic elements are thus integrated into the genome of the host cell as a provirus. When the target cell is an embryo, the cell may then be allowed to develop into a transgenic animal by methods well known in the art.

The recombinant retrovirus used to deliver the RNA coding region is preferably a modified lentivirus, and thus is able to infect both dividing and non-dividing cells. The recombinant retrovirus preferably comprises a modified lentiviral genome that includes an RNA coding region. Further, the modified lentiviral genome preferably lacks endogenous genes for proteins required for viral replication, thus preventing undesired replication, such as replication in the target cells. The required proteins are preferably provided in trans in the packaging cell line during production of the recombinant retrovirus, as described below.

In another embodiment, the recombinant retrovirus used to deliver the RNA coding region is a modified Moloney virus, for example a Moloney Murine Leukemia Virus. In a further embodiment, the virus is a Murine Stem Cell Virus (Hawley, R. G., et al. (1996) Proc. Natl. Acad. Sci. USA 93:10297–10302; Keller, G., et al. (1998).Blood 92:877–887; Hawley, R. G., et al. (1994) Gene Ther. 1:136–138). The recombinant retrovirus also can be a hybrid virus such as that described in Choi, J K; Hoanga, N; Vilardi, A M; Conrad, P; Emerson, S G; Gewirtz, A M. (2001) Hybrid HIV/MSCV LTR Enhances Transgene Expression of Lentiviral Vectors in Human CD34+ Hematopoietic Cells. *Stem Cells* 19, No. 3, 236–246.

In one embodiment the transgene, preferably an RNA coding region, is incorporated into a viral construct that comprises an intact retroviral 5' LTR and a self-inactivating 3' LTR. The viral construct is preferably introduced into a packaging cell line that packages viral genomic RNA based on the viral construct into viral particles with the desired host specificity. Viral particles are collected and allowed to infect the host cell. Each of these aspects is described in detail below.

The Viral Construct

The viral construct is a nucleotide sequence that comprises sequences necessary for the production of recombinant viral particles in a packaging cell. In one embodiment the viral construct additionally comprises genetic elements that allow for the desired expression of a gene of interest in the host.

Generation of the viral construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. (Molecular Cloning: A Laboratory Manual. Cold Spring Harbor Laboratory Press, N.Y. (1989)), Coffin et al. (Retroviruses. Cold Spring Harbor Laboratory Press, N.Y. (1997)) and "RNA Viruses: A Practical Approach" (Alan J. Cann, Ed., Oxford University Press, (2000)).

The viral construct may incorporate sequences from the genome of any known organism. The sequences may be incorporated in their native form or may be modified in any way. For example, the sequences may comprise insertions, deletions or substitutions. In a preferred embodiment the viral construct comprises sequences from a lentivirus genome, such as the HIV genome or the SIV genome. In another preferred embodiment, the viral construct comprises sequences of a murine stem cell virus (MSCV).

The viral construct preferably comprises sequences from the 5' and 3' LTRs of a lentivirus, a moloney murine leukemia virus, a murine stem cell virus or hybrids thereof. In one embodiment, the viral construct comprises the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Preferably the LTR sequences are HIV LTR sequences. The virus also can incorporate sequences from MMV or MSCV.

The viral construct preferably comprises an inactivated or self-inactivating 3' LTR. The 3' LTR may be made self-inactivating by any method known in the art. In one embodiment the U3 element of the 3' LTR contains a deletion of its enhancer sequence, preferably the TATA box, Sp1 and NF-kappa B sites. As a result of the self-inactivating 3' LTR, the provirus that is integrated into the host cell genome will comprise an inactivated 5' LTR.

Optionally, the U3 sequence from the lentiviral 5' LTR may be replaced with a promoter sequence in the viral construct. This may increase the titer of virus recovered from the packaging cell line. An enhancer sequence may also be included. Any enhancer/promoter combination that increases expression of the viral RNA genome in the packaging cell line may be used. In one such embodiment the CMV enhancer/promoter sequence is used (U.S. Pat. No. 5,168,062; Karasuyama et al *J. Exp. Med.* 169:13 (1989).

The viral construct also comprises a transgene. The transgene, may be any nucleotide sequence, including sequences that serve as markers for the provirus. Preferably the transgene comprises one or more RNA coding regions and/or one or more genes of interest.

In the preferred embodiment the transgene comprises at least one RNA coding region. Preferably the RNA coding region is a DNA sequence that can serve as a template for the expression of a desired RNA molecule in the host cell. In one embodiment, the viral construct comprises two or more RNA coding regions.

The viral construct also preferably comprises at least one RNA Polymerase III promoter. The RNA Polymerase III promoter is operably linked to the RNA coding region and can also be linked to a termination sequence. In addition, more than one RNA Polymerase III promoter may be incorporated.

RNA polymerase III promoters are well known to one of skill in the art. A suitable range of RNA polymerase III promoters can be found, for example, in Paule and White. *Nucleic Acids Research.*, Vol 28, pp 1283–1298 (2000), which is hereby incorporated by reference in its entirety. The definition of RNA polymerase III promoters also include any synthetic or engineered DNA fragment that can direct RNA polymerase III to transcribe its downstream RNA coding sequences. Further, the RNA polymerase III (Pol III) promoter or promoters used as part of the viral vector can be inducible. Any suitable inducible Pol III promoter can be used with the methods of the invention. Particularly suited Pol III promoters include the tetracycline responsive promoters provided in Ohkawa and Taira *Human Gene Therapy*, Vol. 11, pp 577–585 (2000) and in Meissner et al. *Nucleic Acids Research*, Vol. 29, pp 1672–1682 (2001), which are incorporated herein by reference.

In one embodiment the viral construct further comprises a gene that encodes a protein that is desirably expressed in one or more of the target cells, for example, a reporter or marker protein. Preferably the gene of interest is located between the 5' LTR and 3' LTR sequences. Further, the gene of interest is preferably in a functional relationship with other genetic elements, for example transcription regulatory sequences such as promoters and/or enhancers, to regulate expression of the gene of interest in a particular manner once the gene of interest is incorporated into the target cell genome. In certain embodiments, the useful transcriptional regulatory sequences are those that are highly regulated with respect to activity, both temporally and spatially.

Preferably the gene of interest is in a functional relationship with an internal Polymerase II promoter/enhancer regulatory sequences. An "internal" promoter/enhancer is one that is located between the 5' LTR and the 3' LTR sequences in the viral construct and is operably linked to the gene that is desirably expressed.

The Polymerase II promoter/enhancer may be any promoter, enhancer or promoter/enhancer combination known to increase expression of a gene with which it is in a functional relationship. A "functional relationship" and "operably linked" mean, without limitation, that the transgene or RNA coding region is in the correct location and orientation with respect to the promoter and/or enhancer that expression of the gene will be affected when the promoter and/or enhancer is contacted with the appropriate molecules.

In another embodiment, the gene of interest is a gene included for safety concerns to allow for the selective killing of the treated target cells within a heterogeneous population, for example within an animal, or more particularly within a human patient. In one such embodiment, the gene of interest is a thymidine kinase gene (TK) the expression of which renders a target cell susceptible to the action of the drug gancyclovir.

In addition, more than one gene of interest may be placed in functional relationship with the internal promoter. For example a gene encoding a marker protein may be placed after the primary gene of interest to allow for identification of cells that are expressing the desired protein. In one embodiment a fluorescent marker protein, preferably green fluorescent protein (GFP), is incorporated into the construct along with the gene of interest. If a second reporter gene is included, an internal ribosomal entry site (IRES) sequence is also preferably included (U.S. Pat. No. 4,937,190). The IRES sequence may facilitate the expression of the reporter gene.

The viral construct may also contain additional genetic elements. The types of elements that may be included in the construct are not limited in any way and will be chosen by the skilled practitioner to achieve a particular result. For example, a signal that facilitates nuclear entry of the viral genome in the target cell may be included. An example of such a signal is the HIV-1 flap signal.

Further, elements may be included that facilitate the characterization of the provirus integration site in the genome of the animal. For example, a tRNA amber suppressor sequence may be included in the construct.

In addition, the construct may contain one or more genetic elements designed to enhance expression of the gene of interest. For example, a woodchuck hepatitis virus responsive element (WRE) may be placed into the construct (Zufferey et al. *J. Virol.* 74:3668–3681 (1999); Deglon et al. *Hum. Gene Ther.*11:179–190 (2000)).

A chicken β-globin insulator (Chung et al. *Proc. Natl. Acad. Sci. USA* 94:575–580 (1997)) may also be included in the viral construct. This element has been shown to reduce the chance of silencing the integrated provirus in a target cell due to methylation and heterochromatinization effects. In addition, the insulator may shield the internal enhancer, promoter and exogenous gene from positive or negative positional effects from surrounding DNA at the integration site on the chromosome.

Any additional genetic elements are preferably inserted 3' of the gene of interest or RNA coding region.

In a specific embodiment, the viral vector comprises: an RNA pol III promoter sequence; the R and U5 sequences from the HIV 5' LTR; the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR.

The viral construct is preferably cloned into a plasmid that may be transfected into a packaging cell line. The preferred plasmid preferably comprises sequences useful for replication of the plasmid in bacteria.

Figure 1B:
FIG. 1B shows a similar construct in which the RNA expression cassettes flank a marker gene.

Schematic diagrams of exemplary retroviral constructs are shown in FIGS. 1A and 1B.

Production of Virus

Any method known in the art may be used to produce infectious retroviral particles whose genome comprises an RNA copy of the viral construct described above.

Preferably, the viral construct is introduced into a packaging cell line. The packaging cell line provides the viral proteins that are required in trans for the packaging of the viral genomic RNA into viral particles. The packaging cell line may be any cell line that is capable of expressing retroviral proteins. Preferred packaging cell lines include 293 (ATCC CCL X), HeLa (ATCC CCL 2), D17 (ATCC CCL 183), MDCK (ATCC CCL 34), BHK (ATCC CCL-10) and Cf2Th (ATCC CRL 1430). The most preferable cell line is the 293 cell line.

The packaging cell line may stably express the necessary viral proteins. Such a packaging cell line is described, for example, in U.S. Pat. No. 6,218,181. Alternatively a packaging cell line may be transiently transfected with plasmids comprising nucleic acid that encodes the necessary viral proteins.

In one embodiment a packaging cell line that stably expresses the viral proteins required for packaging the RNA genome is transfected with a plasmid comprising the viral construct described above.

In another embodiment a packaging cell line that does not stably express the necessary viral proteins is co-transfected with two or more plasmids essentially as described in Yee et al. (*Methods Cell. Biol.* 43A, 99–112 (1994)). One of the plasmids comprises the viral construct comprising the RNA coding region. The other plasmid(s) comprises nucleic acid encoding the proteins necessary to allow the cells to produce functional virus that is able to infect the desired host cell.

The packaging cell line may not express envelope gene products. In this case the packaging cell line will package the viral genome into particles that lack an envelope protein. As the envelope protein is responsible, in part, for the host range of the viral particles, the viruses are preferably pseudotyped. Thus the packaging cell line is preferably transfected with a plasmid comprising sequences encoding a membrane-associated protein that will permit entry of the virus into a host cell. One of skill in the art will be able to choose the appropriate pseudotype for the host cell that is to be used. For example, in one embodiment the viruses are pseudotyped with the vesicular stomatitis virus envelope glycoprotein (VSVg). In addition to conferring a specific host range this pseudotype may permit the virus to be concentrated to a very high titer. Viruses can alternatively be pseudotyped with ecotropic envelope proteins that limit infection to a specific species, such as mice or birds. For example, in another embodiment, a mutant ecotropic envelope protein is used, such as the ecotropic envelope protein 4.17 (Powell et al. Nature Biotechnology 18(12):1279–1282 (2000)).

In the preferred embodiment a packaging cell line that does not stably express viral proteins is transfected with the viral construct, a second vector comprising the HIV-1 packaging vector with the env, nef, 5'LTR, 3'LTR and vpu sequences deleted, and a third vector encoding an envelope glycoprotein. Preferably the third vector encodes the VSVg envelope glycoprotein.

If the viral construct described above comprises siRNA that is directed against a cellular gene or a viral gene, particularly an essential gene such as a gene involved in the virus life cycle, viral production in the packaging cells may be severely reduced. Thus, in another embodiment of invention, RNA interference activity in the packaging cells is suppressed to improve the production of recombinant virus. By suppressing RNA interference in the packaging cell line, sufficient quantities of recombinant retrovirus that expresses siRNA targeting essential genes, such as Cis-regulatory elements required for the HIV-1 life cycle, can be produced to facilitate its therapeutic use.

Suppression of siRNA activity that reduces virus production may be accomplished, for example, by interfering with one or more components necessary for RNA interference. Such components include, for example, molecules in the pathway by which inactive, hairpin precursor siRNAs are processed into open-ended double-stranded mature siRNAs and molecules involved in the formation and function of the RNA-Induced-Silencing-Complex (RISC), which is essential for target RNA degradation. Exemplary components necessary for RNA interference include, but are not limited to RNase III family members such as Dicer-1 and Dicer-2 (Hammond et al. Nat. Rev. Genet. 2:110–119 (2001)), Dicer associated proteins such as FMR1 (Ishizuka et al. Genes Dev. 16:2497–2508 (2002); Caudy et al. Genes Dev. 16:2491–2496 (2002)), Argonaute proteins including members of the Ago1 subfamily of Argonaute proteins (Carmell et al. Genes Dev. 16(21):2733–2742 (2002)) such as eIF2C2, eIF2C1 (GERp95)/hAgo1, eIF2C2/ hAgo2, hAgo3, hAgo4 and hAgo 5, members of the Piwi subfamily of Argonaute proteins (Carmell et al. Genes Dev. 26:2733–2742 (2002)) such as Hiwi1/Miwi1, Hiwi2/ Miwi2 and Hili/Mili, which are required for the assembly and activity of RISC (Mourelatos et al. Genes Dev. 16(6):720–7728 (2002); Carmell et al. Genes Dev. 16(21):2733–2742 (2002)), RNA helicases such as Gemin3 (Mourelatos et al. Genes Dev. 16(6): 720–728 (2002)) and P678 helicase (Ishizuka et al., supra) and other RISC/miRNP associated proteins such as Gemin2, Gemin4, P115/ slicer and VIG (Mourelatos et al. Genes Dev. 16(6):720–728 (2002); Schwarz and Zamore Genes Dev. 16:1025–1031 (2002); Caudy et al. Genes Dev. 16:2491–2496 (2002)). However, any component that is known in the art to be necessary for full siRNA activity may be targeted.

Suppression of RNA interference activity may be accomplished by any method known in the art. This includes, without limitation, the cotransfection or stable transfection of constructs expressing siRNA molecules in packaging cells to inhibit molecules that play a role in RNA interference.

In one embodiment production of virus from the packaging cell line is increased by cotransfection of one or more vectors that express an siRNA molecule that inhibits RNA interference, such as an siRNA molecule that inhibits Dicer activity and/or eIF2C2 activity. In a preferred embodiment, a packaging cell line is created that stably expresses one or more molecules that inhibit RNA interference, such as siRNAs that inhibit Dicer activity and/or eIF2C2 activity.

The recombinant virus is then preferably purified from the packaging cells, titered and diluted to the desired concentration.

Delivery of the Virus

The virus may be delivered to the cell in any way that allows the virus to infect the cell. Preferably the virus is allowed to contact the cell membrane. A preferred method of delivering the virus to mammalian cells is through direct contact.

In one embodiment, the target cells are preferably contacted with the virus in culture plates. The virus may be suspended in media and added to the wells of a culture plate. The media containing the virus may be added prior to the plating of the cells or after the cells have been plated. Preferably cells are incubated in an appropriate amount of media to provide viability and to allow for suitable concentrations of virus in the media such that infection of the host cell occurs.

The cells are preferably incubated with the virus for a sufficient amount of time to allow the virus to infect the cells. Preferably the cells are incubated with virus for at least 1 hour, more preferably at least 5 hours and even more preferably at least 10 hours.

In any such embodiments, any concentration of virus that is sufficient to infect the cell may be used. When the target cell is to be cultured, the concentration of the viral particles is at least 1 pfu/µl, more preferably at least 10 pfu/µl, even more preferably at least 400 pfu/µl and even more preferably at least $1 \times 10^4$ pfu/µl.

Following infection with the virus, the cells can be introduced into an animal. The location of introduction of cultured cells will depend on the cell type used. For example, when the cells are hematopoietic cells, the cells can be introduced into the peripheral blood stream. The cells introduced into an animal are preferably cells derived from that animal, to avoid an adverse immune response. Cells also can be used that are derived from a donor animal having a similar immune makeup. Other cells also can be used, including those designed to avoid an immunogenic response.

In another embodiment, a suitable amount of virus is introduced into an animal directly, for example though injection into the body. In one such embodiment, the viral particles are injected into the animal's peripheral blood stream. Other injection locations also are suitable. Depending on the type of virus, introduction can be carried out through other means including for example, inhalation, or direct contact with epithelial tissues, for example those in the eye, mouth or skin.

The cells and animals incorporating introduced cells may be analyzed, for example for integration of the RNA coding region, the number of copies of the RNA coding region that integrated, and the location of the integration. Such analysis may be carried out at any time and may be carried out by any methods known in the art. Standard techniques are described, for example, in Hogan et al. (supra).

The methods of infecting cells disclosed above do not depend upon species-specific characteristics of the cells. As a result, they are readily extended to all mammalian species.

As discussed above, the modified retrovirus can be pseudotyped to confer upon it a broad host range. One of skill in the art would also be aware of appropriate internal promoters to achieve the desired expression of a gene of interest in a particular animal species. Thus, one of skill in the art will be able to modify the method of infecting cells derived from any species.

Down-Regulating Gene Expression in a Target Cell

The methods described herein allow the expression of RNA molecules in cells, and are particularly suited to the expression of small RNA molecules, which can not be readily expressed from a Pol II promoter. According to a preferred embodiment of the invention, an RNA molecule is expressed within a cell in order to down-regulate the expression of a target gene. The ability to down-regulate a target gene has many therapeutic and research applications, including identifying the biological functions of particular genes. Using the techniques and compositions of the invention, it will be possible to knock-down (or down-regulate) the expression of a large number of genes, both in cell culture and in mammalian organisms. In particular, it is desirable to down-regulate genes in a target cell that are necessary for the life cycle of a pathogen, such as a pathogenic virus.

In preferred embodiments of the invention, an RNA expression cassette comprises a Pol III promoter and an RNA coding region. The RNA coding region preferably encodes an RNA molecule that is capable of down-regulating the expression of a particular target gene or genes. The RNA molecule encoded can, for example, be complementary to the sequence of an RNA molecule encoding a gene to be down-regulated. In such an embodiment, the RNA molecule is designed to act through an antisense mechanism.

A more preferred embodiment involves the expression of a double-stranded RNA complex, or an RNA molecule having a stem-loop or a so-called "hairpin" structure. As used herein, the term "RNA duplex" refers to the double stranded regions of both the RNA complex and the double-stranded region of the hairpin or stem-lop structure. An RNA coding region can encode a single stranded RNA, two or more complementary single stranded RNAs or a hairpin forming RNA.

Double stranded RNA has been shown to inhibit gene expression of genes having a complementary sequence through a process termed RNA interference or suppression (see, for example, Hammond et al. Nat. Rev. Genet. 2:110–119 (2001)).

According to the invention, the RNA duplex or siRNA corresponding to a region of a target gene to be down-regulated is expressed in the cell. The RNA duplex is substantially identical (typically at least about 80% identical, and more typically at least about 90% identical) in sequence to the sequence of the gene targeted for down regulation. siRNA duplexes are described, for example, in Bummelkamp et al. Science 296:550–553 (2202), Caplen et al. Proc. Natl. Acad. Sci. USA 98:9742–9747 (2001) and Paddison et al. Genes & Devel. 16:948–958 (2002).

The RNA duplex is generally at least about 15 nucleotides in length and is preferably about 15 to about 30 nucleotides in length. In some organisms, the RNA duplex can be significantly longer. In a more preferred embodiment, the RNA duplex is between about 19 and 22 nucleotides in length. The RNA duplex is preferably identical to the target nucleotide sequence over this region.

When the gene to be down regulated is in a family of highly conserved genes, the sequence of the duplex region can be chosen with the aid of sequence comparison to target only the desired gene. If there is sufficient identity among a family of homologous genes within an organism, a duplex region can be designed that would down regulate a plurality of genes simultaneously.

Figure 2:
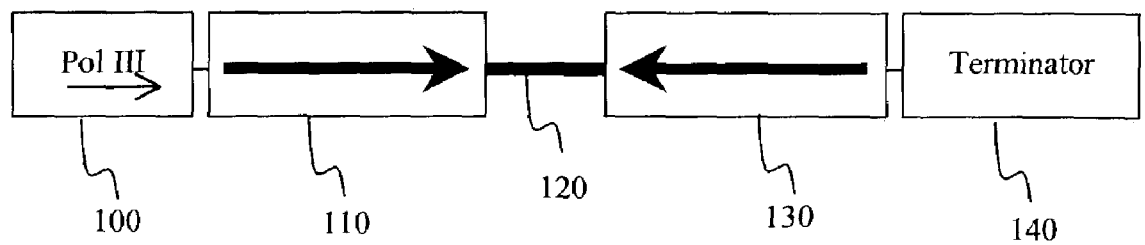
FIG. 2 shows a schematic view of an RNA expression cassette having a RNA polymerase III promoter 100 linked to an siRNA region 110–130, having a sense region 110, a loop region 120, and an antisense region 130, and a terminator sequence 140.

The duplex RNA can be expressed in a cell from a single retroviral construct. In the preferred embodiment, a single RNA coding region in the construct is a serves as a template for the expression of a self-complementary hairpin RNA, comprising a sense region, a loop region and an antisense region. This embodiment is illustrated in FIG. 2, which shows a schematic view of an RNA expression cassette having an RNA Pol III promoter 100 operatively linked to an RNA coding region, having a sense region 110, a loop region 120, an antisense region 130 and a terminator region 140. The sense 110 and antisense 130 regions are each preferably about 15 to about 30 nucleotides in length. The loop region 120 preferably is about 2 to about 15 nucleotides in length, more preferably from about 4 to about 9 nucleotides in length. Following expression the sense and antisense regions form a duplex.

Figure 3:
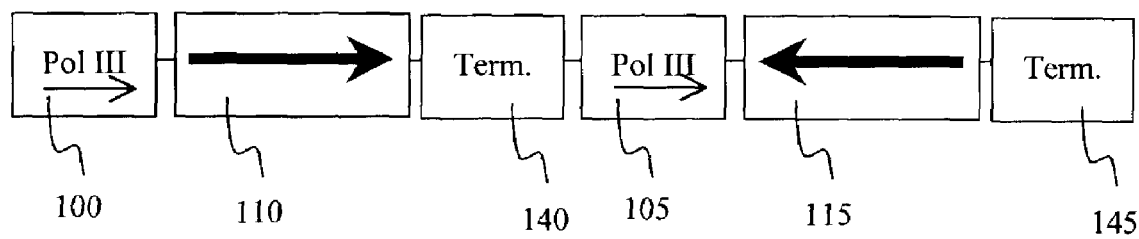
FIG. 3 shows a schematic view of an RNA expression cassette having a RNA polymerase III promoter 100 linked to a first RNA coding region 110 and a first terminator sequence 140 and a second RNA polymerase III promoter 105 linked to a second RNA coding region 115 and a second terminator 145.

In another embodiment, the retroviral construct comprises two RNA coding regions. The first coding region is a template for the expression of a first RNA and the second coding region is a template for the expression of a second RNA. Following expression, the first and second RNA's form a duplex. The retroviral construct preferably also comprises a first Pol III promoter operably linked to the first RNA coding region and a second Pol III promoter operably linked to the second RNA coding region. This embodiment is illustrated in FIG. 3, which shows a schematic view of an RNA expression cassette having an RNA Polymerase III promoter 100 linked to a first RNA coding region 110 and a first terminator sequence 140 and a second RNA polymerase III promoter 105 linked to a second RNA coding region 115 and a second terminator 145.

Figure 4:
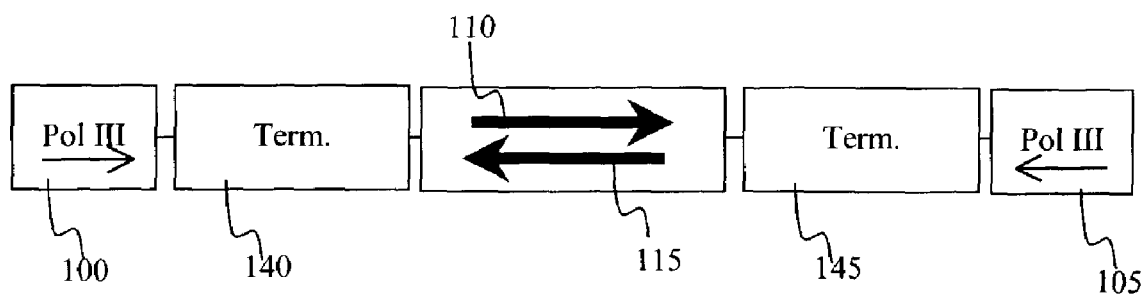
FIG. 4 shows a schematic view of an RNA expression cassette having a first RNA polymerase III promoter 100 linked to an RNA coding region 110 and a first terminator sequence 145. The expression cassette has a second RNA polymerase III promoter 105 linked to the RNA coding region 115, the same sequence as 110 in reverse, and a second terminator 140.

In yet another embodiment of the invention, the retroviral construct comprises a first RNA Pol III promoter operably linked to a first RNA coding region, and a second RNA Pol III promoter operably linked to the same first RNA coding region in the opposite direction, such that expression of the RNA coding region from the first RNA Pol III promoter results in a synthesis of a first RNA molecule as the sense strand and expression of the RNA coding region from the second RNA Pol III promoter results in synthesis of a second RNA molecule as an antisense strand that is substantially complementary to the first RNA molecule. In one such embodiment, both RNA Polymerase III promoters are separated from the RNA coding region by termination sequences, preferably termination sequences having five consecutive T residues. FIG. 4 shows a schematic view of an RNA expression cassette having a first RNA Polymerase III promoter 100 linked to an RNA coding region 110 and a first terminator sequence 145. The expression cassette has a second RNA polymerase III promoter 105 linked to the RNA coding region 115, the same sequence as 110 in reverse, and a second terminator 140.

In further embodiments an RNA duplex is expressed using two or more retroviral constructs. In one embodiment, a first retroviral construct is used that directs the expression of a first RNA and a second retroviral construct is used that directs expression of a second RNA that is complementary to the first. Following expression the first and second RNAs form a duplex region. It is preferred, however, that the entire duplex region is introduced using retroviral particles derived from a single retroviral construct. As discussed above, several strategies for expressing a duplex RNA from a single viral construct are shown in FIGS. 2-4.

The RNA duplexes may be flanked by single stranded regions on one or both sides of the duplex. For example, in the case of the hairpin, the single stranded loop region would connect the duplex region at one end.

The RNA coding region is generally operatively linked to a terminator sequence. The pol III terminators preferably comprise of stretches of 4 or more thymidine ("T") residues. In a preferred embodiment, a cluster of 5 consecutive Ts is linked immediately downstream of the RNA coding region to serve as the terminator. In such a construct pol III transcription is terminated at the second or third T of the DNA template, and thus only 2 to 3 uridine ("U") residues are added to the 3' end of the coding sequence.

The sequence of the RNA coding region, and thus the sequence of the RNA duplex, preferably is chosen to be complementary to the sequence of a gene whose expression is to be downregulated in a cell or organism. The degree of down regulation achieved with a given RNA duplex sequence for a given target gene will vary by sequence. One of skill in the art will be able to readily identify an effective sequence. For example, in order to maximize the amount of suppression, a number of sequences can be tested in cell culture prior to treating a target cell or generating a transgenic animal. As an understanding of the sequence requirements for RNA interference is determined, the RNA duplex can be selected by one of skill in the art.

Inhibition of Viral Replication and/or Gene Expression in a Target Cell

According to one aspect of the invention, the target of the RNA duplex is a sequence that is necessary for the life cycle or replication of a virus, including for example, gene expression of the virus and the expression of a cellular receptor or co-receptor necessary for viral replication. In one embodiment of the invention, the virus to be inhibited is the human immunodeficiency virus (HIV). In particular embodiments the target sequence is selected from the group consisting of Rev, Gag, Pol, LTRs, TAR, RRE, ψ, att, pbs, ppt and other essential DNA and RNA cis-regulatory elements.

The invention also includes methods of treating a patient having a viral infection. In one embodiment the method comprises administering to the patient an effective amount of a recombinant retroviral particle (or particles) encoding at least one double stranded RNA having at least 90% homology and preferably identical to a region of at least about 15 to 25 nucleotides in a nucleotide that is important for normal viral replication. For example, the double stranded RNA may have homology to a nucleic acid in a viral genome, a viral gene transcript or in a gene for a patient's cellular receptor that is necessary for the life cycle of the virus.

In one embodiment, the patient to be treated is infected with the human immunodeficiency virus. A target cell is removed from a patient prior to treatment with the recombinant virus particle. In a preferred embodiment, the target cell is a CD34-positive hematopoietic stem cell. Such stem cells can be purified by one of skill in the art. Methods for such purification are known and taught for example in U.S. Pat. Nos. 4,965,204; 4,714,680; 5,061,620; 5,643,741; 5,677,136; 5,716,827; 5,750,397 and 5,759,793. One method for purifying such CD34-positive stem cells involves centrifugation of peripheral blood samples to separate mononuclear cells and granulocytes and sorting by fluorescence activated cell sorting (FACS). Sorted cells can be enriched for CD34+ cells through any of the above techniques. In a particular embodiment, the cells are enriched for CD34+ cells through a magnetic separation technology such as that available from Miltenyi Biotec and described in the following publications: Köogler et al. (1998) Bone Marrow Transplant. 21: 233–241; Pasino et al. (2000) Br. J. Haematol. 108: 793–800. The isolated CD34-positive stem cell is treated with a recombinant retroviral particle having an RNA coding region encoding a double stranded RNA directed against one or more targets within the viral genome and/or cellular targets that are necessary for the viral life cycle, including, for example, receptors or co-receptors necessary for entry of the pathogenic virus. The treated stem cells are then reintroduced into the patient.

The methods of the invention can be used to treat a variety of viral diseases, including, for example, human immunodeficiency virus (HIV-1 and HIV-2), hepatitis A, hepatitis B, hepatitis C.

It is also possible to treat a patient with an anti-viral recombinant retrovirus in order to confer immunity or increased resistance for the patient to a desired pathogen, such as a virus.

Cellular Targets

According to the invention, one of skill in the art can target a cellular component, such as an RNA or an RNA encoding a cellular protein necessary for the pathogen life cycle, particularly a viral life cycle. In a preferred embodiment, the cellular target chosen will not be a protein or RNA that is necessary for normal cell growth and viability. Suitable proteins for disrupting the viral life cycle include, for example, cell surface receptors involved in viral entry, including both primary receptors and secondary receptors, and transcription factors involved in the transcription of a viral genome, proteins involved in integration into a host chromosome, and proteins involved in translational or other regulation of viral gene expression.

A number of cellular proteins are known to be receptors for viral entry into cells. Some such receptors are listed in an article by E. Baranowski, C. M. Ruiz-Jarabo, and E. Domingo, "Evolution of Cell Recognition by Viruses," *Science*

292: 1102–1105, which is hereby incorporated by reference in its entirety. Some cellular receptors that are involved in recognition by viruses are listed below: Adenoviruses: CAR, Integrins, MHC I, Heparan sulfate glycoaminoglycan, Siliac Acid; Cytomegalovirus: Heparan sulfate glycoaminoglycan; Coxsackieviruses: Integrins, ICAM-1, CAR, MHC I; Hepatitis A: murine-like class I integral membrane clycoprotein; Hepatitis C: CD81, Low density lipoprotein receptor; HIV (Retroviridae): CD4, CXCR4, Heparan sulfate glycoaminoglycan; HSV: Heparan sulfate glycoaminoglycan, PVR, HveB, HveC; Influenza Virus: Sialic acid; Measles: CD46, CD55; Poliovirus,: PVR, HveB, HveC; Human papillomavirus: Integrins. One of skill in the art will recognize that the invention is not limited to use with receptors that are currently known. As new cellular receptors and co-receptors are discovered, the methods of the invention can be applied to such sequences.

Human Immunodeficiency Virus (HIV)

HIV Viral Targets:

In one embodiment of the invention, the retroviral construct has an RNA coding region that encodes a double stranded molecule having at least 90% homology to the HIV viral RNA genome, an expressed region of the HIV viral genome, for example, to any region of about 19–25 nucleotides in length of the 9-kb transcript of the integrated HIV virus, or any of the variously spliced mRNA transcripts of HIV (Schwartz, S; Felber, B K; Benko, D M; Fenya, E M; Pavlakis, G N. Cloning and functional analysis of multiply spliced mRNA species of human immunodeficiency virus type 1. *J. Virol.* 1990; 64(6): 2519–29). Target regions within the HIV transcripts can be chosen to correspond to any of the viral genes, including, for example, HIV-1 LTR, vif, nef, and rev. In another embodiment, the RNA coding region encodes a double stranded region having at least 90% homology to a receptor or co-receptor of the HIV virus. For example, the primary receptor for HIV entry into T cells is CD4. In a preferred embodiment, the co-receptors CXC chemokine receptor 4 (CXCR4) and CC chemokine receptor 5 (CCR5) are down-regulated according to the methods of the invention. CXCR4 (Feddersppiel et al. Genomics 16:707–712 (1993)) is the major co-receptor for T cell trophic strains of HIV while CCR5 (Mummidi et al. J. Biol. Chem. 272: 30662–30671 (1997)) is the major co-receptor for macrophage trophic strains of HIV. Other cellular targets against HIV include the RNA transcripts for proteins involved in the HIV life cycle, including cyclophilin, CRM-1, importin-β, HP68 (Zimmerman C, et al. Identification of a host protein essential for assembly of immature HIV-1 capsids. *Nature* 415 (6867): 88–92 (2002)) and other as yet unknown cellular factors.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

All patent and literature references cited in the present specification are hereby incorporated by reference in their entirety.

EXAMPLES

Example 1

Figure 5:
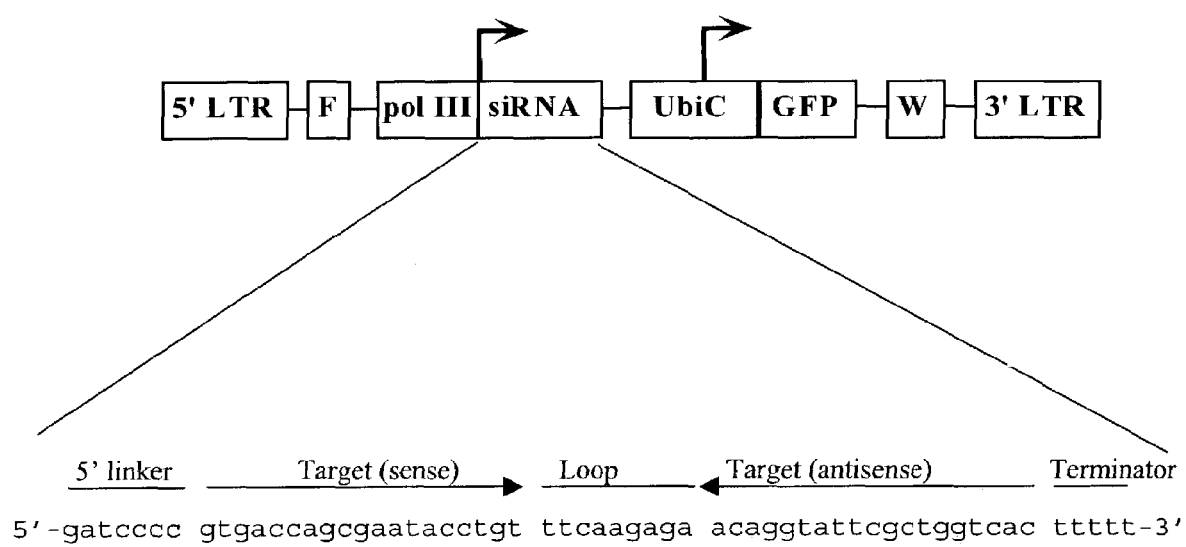
FIG. 5. Schematic illustration of a lacZ siRNA encoding lentiviral vector. 5. 'LTR: an HIV based lentiviral vector 5' LTR; F: an HIV Flap element; pol III: a human H1-RNA pol III promoter (−240 to −8); siRNA: a lacZ specific small hairpin RNA coding region and its structure and detailed sequence are illustrated below. UbiC: an internal human ubiquitinC promoter; GFP: a GFP marker gene driven by UbiC promoter. W: a woodchuck RNA regulatory element. 3'LTR: an HIV based self inactivating lentiviral 3' LTR.

According to this example, an siRNA lentiviral construct against lacZ gene was constructed by insertion of the siRNA expression cassette into the PacI site of HC-FUGW vector (FIG. 5). HC-FUGW vector (SEQ ID NO: 3) contains a GFP marker gene driven by human Ubiquitin promoter for tracking transduction events. The vector also contains an HIV DNA Flap element to improve the virus titers, and WPRE for high level expression of viral genes. The siRNA expression cassette is composed of a pol III promoter and a small hairpin RNA coding region followed by a pol III terminator site. The pol III promoter is derived from −240 to −8 region of human H1-RNA promoter and is connected to the downstream RNA coding region through a 7 base pair linker sequence to ensure that the transcription is precisely initiated at the first nucleotide of the RNA coding sequence. The small hairpin RNA coding region contains a 19 nt sequence corresponding to 1915–1933 region of the sense strand of lacZ gene coding sequence and the 19 nt perfect reverse complementary sequence separated by a 9 nt loop region. The terminator is comprised of 5 consecutive thymidine residues linked immediately downstream of the RNA coding sequence.

Example 2

Figure 6:
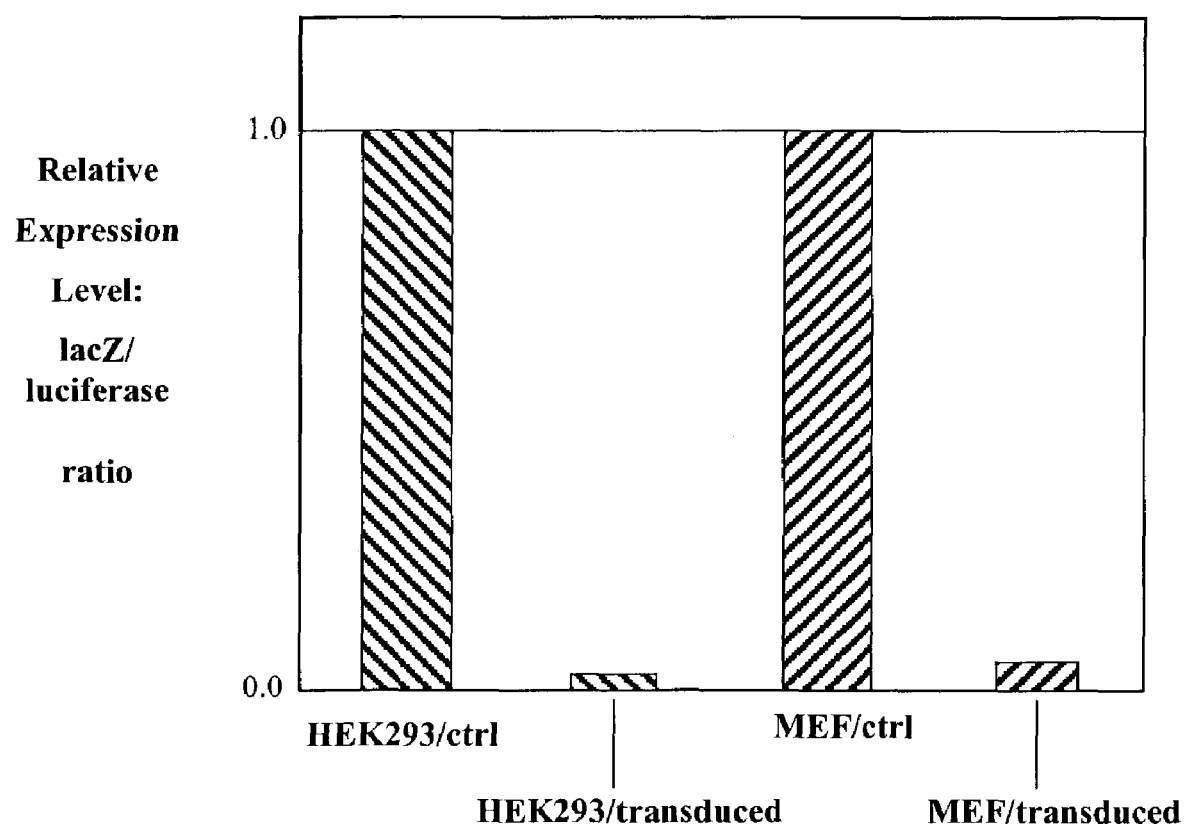
FIG. 6. A lacZ specific siRNA encoded by a lentiviral vector can efficiently inhibit the expression of lacZ reporter gene in virus transduced mammalian cells. MEF: mouse embryonic fibroblasts; HEK293: human embryonic kidney cells. Both of the test cell lines harbor lacZ and firefly luciferase reporter genes, and the expression levels of the reporter genes can be measured by chemiluminescent assays. Ctrl: the ratio of lacZ activity versus Luc activity of the uninfected parental cells, which was arbitrarily set to 1. Transduced: the specific inhibition of lacZ expression calculated as the reduction of lacZ to Luc ratio.

This example demonstrates the transduction of cultured mammalian cells with a retroviral vector (FIG. 6). The retroviral vector encoding a small hairpin RNA molecule described in Example 1, was used to transfect cultured mammalian cells that express lacZ, and caused a profound decrease in the expression of the test gene lacZ. The lacZ siRNA virus was produced by cotransfection of the retroviral vector, a helper virus plasmid (pRSV-Rev) and VSVg expression plasmid in HEK293 cells. The virus particles were harvested from the cell culture supernatants and concentrated by ultracentrifugation. The concentrated virus preparations were used to infect either mouse embryonic fibroblasts (MEF) or HEK293 cells which harbor both lacZ and firefly luciferase (Luc) reporter genes. Infection was monitored by the GFP signal which is expressed from the marker gene cassette of the viral vector. Under the conditions of this experiment, >98% of the test cells were GPF+ and thus successfully transduced. The expression levels of lacZ and Luc reporter genes were measured by chemiluminescent assays using commercially available kits (lacZ assay kit from Roche and Luc from Promega). The lacZ siRNA virus only inhibited the expression of lacZ but not Luc. The specific inhibition was determined by the ration of lacZ activity versus Luc activity. The lacZ/Luc ration of the uninfected parental cells was arbitrarily set to 1 and the values of the infected cells were calculated accordingly. As shown in FIG. 6, transfection with the virus resulted in dramatic reduction in the amount of expression of the lacZ gene in both MEK and HEK293 cells.

Figure 8:
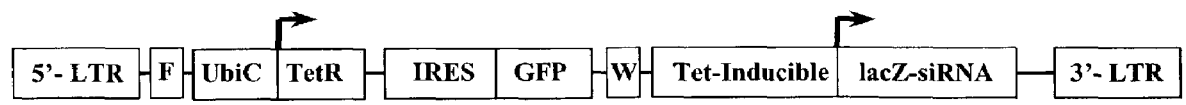
FIG. 8 shows a schematic illustration of a Tet-inducible lacZ siRNA lentiviral vector. A Tet repressor gene (TetR; SEQ ID NO: 7) is the under the control human UbiquitinC promoter and its expression can be monitored by the downstream GFP marker coupled by IRES element (internal ribosomal entry site). The anti-lacZ siRNA cassette is driven by a Tet-inducible pol III promoter derived from human U6-promoter (−328 to +1) containing a single TetR binding site (TetO1) between the PSE and TATA box (SEQ ID NO: 6). In the absence of tetracycline, TetR binds to the promoter and its expression is repressed. Upon the addition of tetracycline, TetR is moved from the promoter and transcription starts.

A tet-iducible lacZ siRNA lentiviral vector was also prepared as illustrated in FIG. 8. A Tet repressor gene (TetR; SEQ ID NO: 7) was placed the under the control of the human UbiquitinC promoter so that its expression could be monitored by the downstream GFP marker. The anti-lacZ siRNA cassette was driven by a Tet-inducible pol III promoter derived from human U6-promoter (−328 to +1) containing a single TetR binding site (TetO1) between the PSE and TATA box (SEQ ID NO: 6). The TetR coding sequence was PCR amplified from genomic DNA from the TOP10 strain of *E. coli* adn cloned into a modified version of FUIGW as a Bgl2-EcoR1 fragment. In the absence of tetracycline, TetR binds to the promoter and its expression is repressed. Upon the addition of tetracycline, TetR is moved from the promoter and transcription starts.

Figure 9:
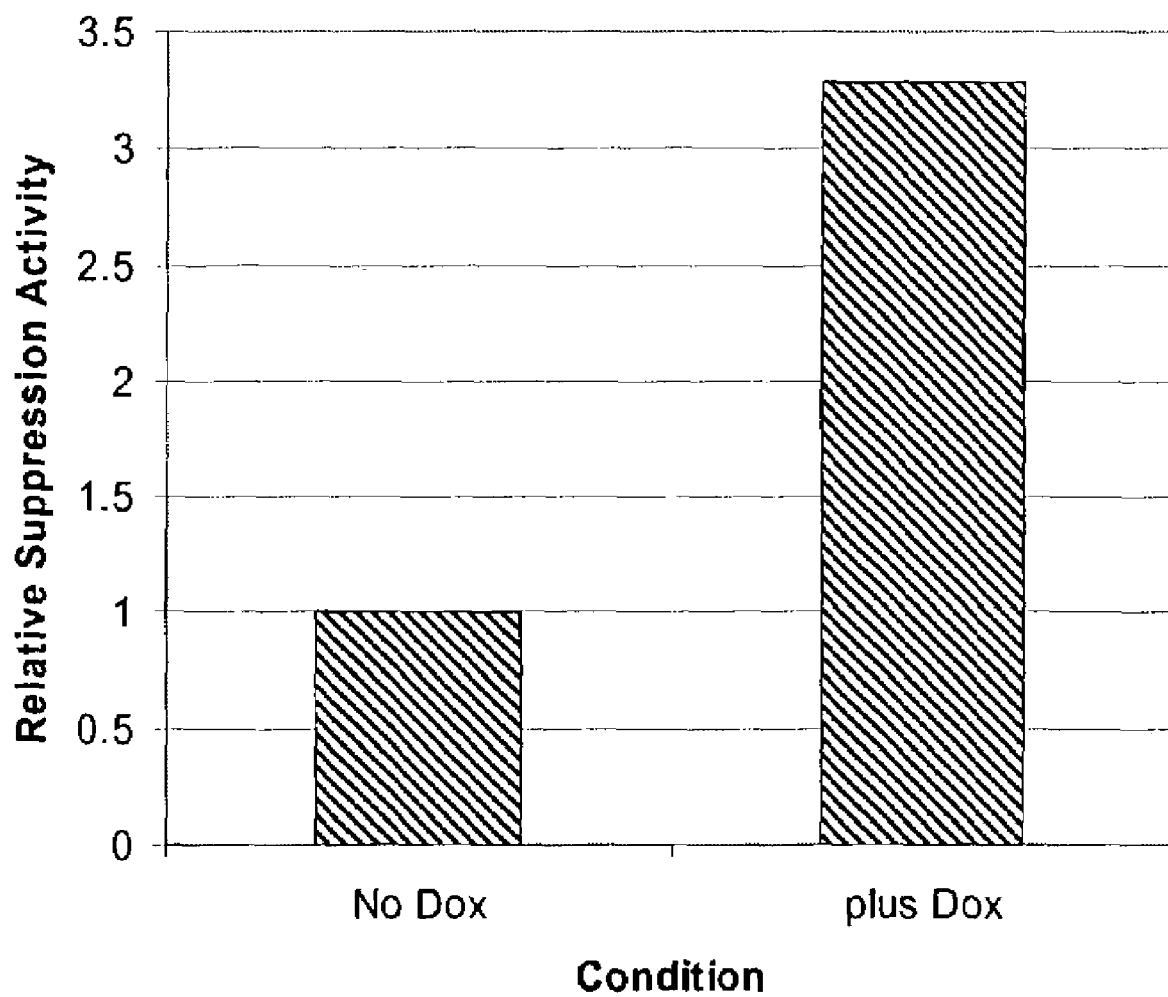
FIG. 9 shows the results of an experiment that demonstrated that a Tet-inducible siRNA expression cassette can regulate gene expression in response to Doxycycline treatment. lacZ and luciferase double expressing HEK293 cells (293Z+Luc) were transduced with a lentiviral vector carrying a Tet-inducible lacZ-siRNA cassette and a Tet repressor under the control of a UbiquitinC promoter (FIG. 8). The transduced cells were treated with 10 ug/ml Doxycycline (Plus Dox) for 48 hr or without the Doxycycline treatment as a control (No Dox). LacZ and luciferase activities were measured as described in the previous figures. The relative suppression activity is calculated as the ratio of lacZ versus luciferase and No Dox control was arbitrarily set to 1.

The Tet-inducible siRNA expression cassette was able to regulate gene expression in response to Doxycycline treatment. Virus was prepared from the retroviral construct carrying the Tet-inducible lacZ-siRNA cassette and a Tet repressor under the control of a UbiquitinC promoter and used to transduce HEK293 cells expressing both lacZ and luciferase (293Z+Luc). The transduced cells were treated with 10 ug/ml Doxycycline (Plus Dox) for 48 hr or without the Doxycycline treatment as a control (No Dox). LacZ and luciferase activities were measured as described in the previous figures. The relative suppression activity is calculated as the ratio of lacZ versus luciferase and No Dox control was arbitrarily set to 1. As can be seen in FIG. 9, in the presence of doxycycline suppression of lacZ activity was significantly enhanced.

Example 3

Figure 7:
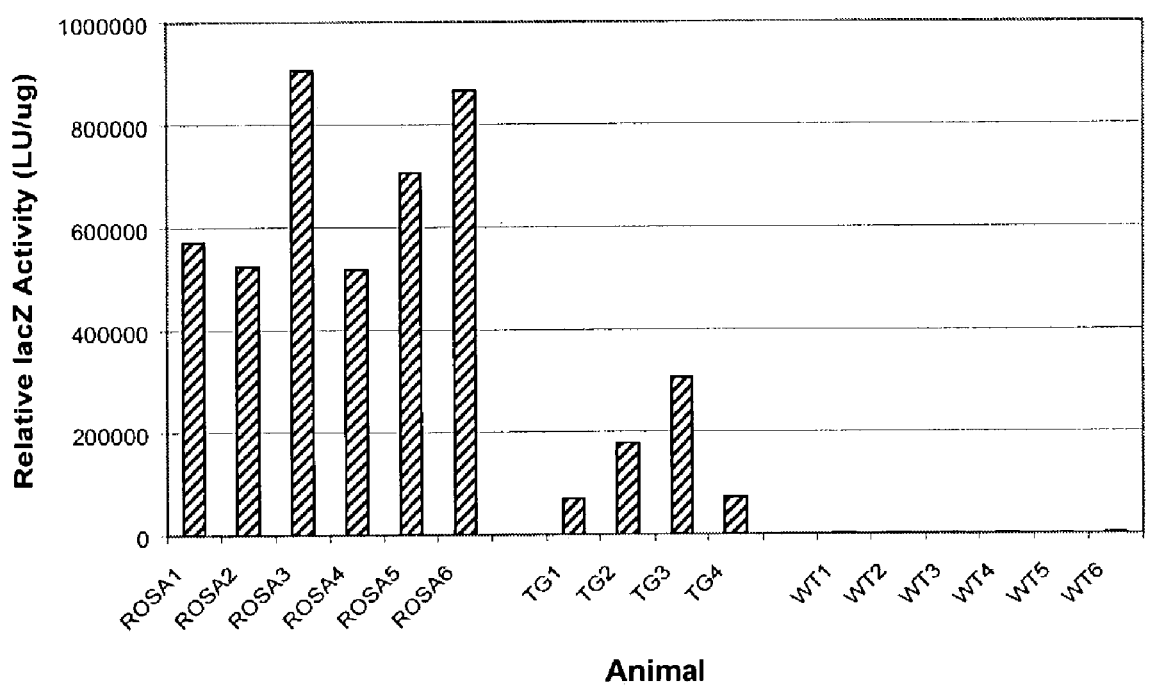
FIG. 7. Transgenic animals that express a lacZ specific siRNA molecule encoded by a lentiviral vector can successfully suppress the expression of the ubiquitous lacZ reporter gene in a ROSA26± background. ROSA1–6: the lacZ activities in the limb tissues of six E17.5 ROSA26± embryos which served as positive controls. The difference in lacZ activity between individual ROSA26± embryos may result from variable protein extraction efficiency. TG1–4: the lacZ activities in the limb tissues of four E17.5 transgenic embryos expressing a lentiviral vector-encoded lacZ siRNA molecule in ROSA± background. WT1–6: lacZ activity in the limb tissues of six E17.5 C57B1/6 wildtype embryos, included as the negative control. The background levels of endogenous beta-galactosidase activity are general below 1,000 LU/ug, thus the columns are not visible.

This example demonstrates the generation of transgenic animals that express an siRNA molecule encoded by a lentiviral vector. The expression of the lacZ specific siRNA construct described in Example 1 resulted in extensive suppression of lacZ activity in ROSA26+/− mice. ROSA26+/− animals carry one copy of an ubiquitously expressed lacZ reporter gene. The lacZ siRNA virus preparations described in Example 2 were used for perivitelline injection of ROSA26+/− single cell embryos obtained from hormone primed C57Bl/6 female donors×ROSA26+/+ stud males. The injected single cell embryos were subsequently transferred into the oviduct of timed pseudopregnant female recipients. Embryonic day 15.5 to 17.5 (E15.5–17.5) fetuses were recovered from the surrogate mothers. Successful transgenesis was scored by positive GFP signal observed with the fetuses under fluorescent microscope. Protein extracts prepared from the limb tissues of the fetuses were used for the LacZ chemiluminescent assay according to the manufacturer's instruction (Roche), and protein concentrations of the tissue extracts were determined by the Bradford assay (BioRad). The lacZ expression levels were expressed as light units (LU) per ug of proteins (LU/ug). The E15.5–17.5 fetuses from the timed mating of C57Bl/6 females×ROSA 26+/+ males and C57Bl/6 females×C57Bl/6 males were served as the positive and negative controls respectively. The results are shown in FIG. 7. In animals G1–G4 (those treated with lentiviral vetor encoding the siRNA construct), the animals showed markedly decreased expression of the lacZ gene as compared with untreated control animals.

Example 4

Figure 10:
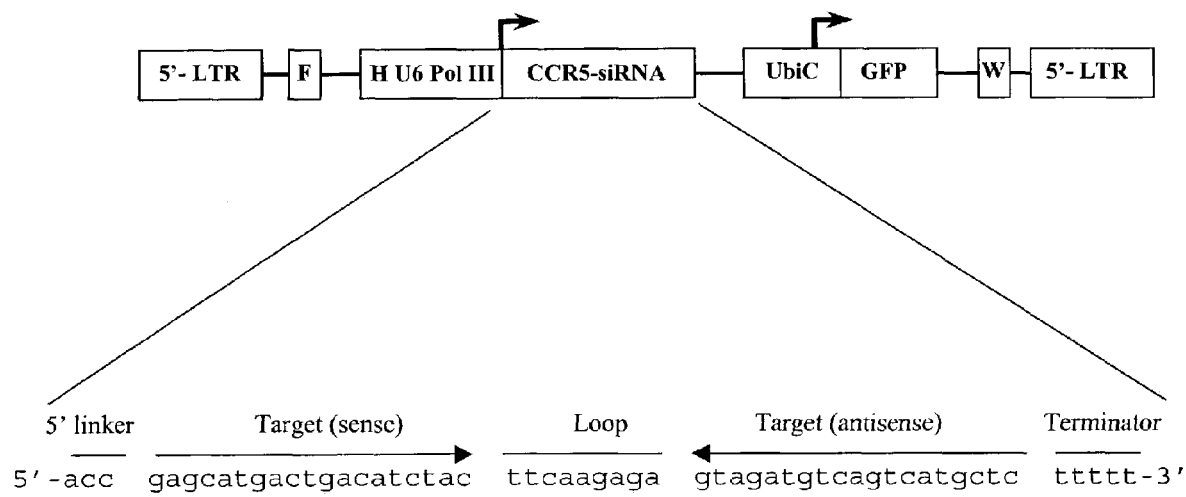
FIG. 10 shows a schematic illustration of an anti-human CCR5 siRNA encoding lentiviral vector. 5'LTR: an HIV based lentiviral vector 5' LTR; F: an HIV Flap element; a human U6-RNA pol III promoter (−328 to +1); siRNA: a human CCR5 specific short hairpin cassette and its structure and detailed sequence are illustrated below. UbiC: an internal human ubiquitinC promoter; GFP: a GFP marker gene driven by UbiC promoter. W: a woodchuck RNA regulatory element. 3'LTR: an HIV based self-inactivating lentiviral 3' LTR.

A lentiviral construct comprising an RNA coding region encoding an anti-human CCR5 siRNA was prepared. As illustrated in FIG. 10, the vector comprised an HIV based lentiviral vector 5' LTR, an HIV Flap element, a human U6RNA pol II promoter (−328 to +1; SEQ ID NO: 4), a human CCR5 specific short hairpin RNA cassette, an internal ubiquitin promoter, a GFP marker gene operably linked to the ubiquitin promoter a WRE regulatory element and an HIV based self-inactivating lentiviral 3, LTR. The structure and sequence of the anti-CCR5 siRNA are provided in FIG. 10 and SEQ ID NO: 1.

Figure 11:
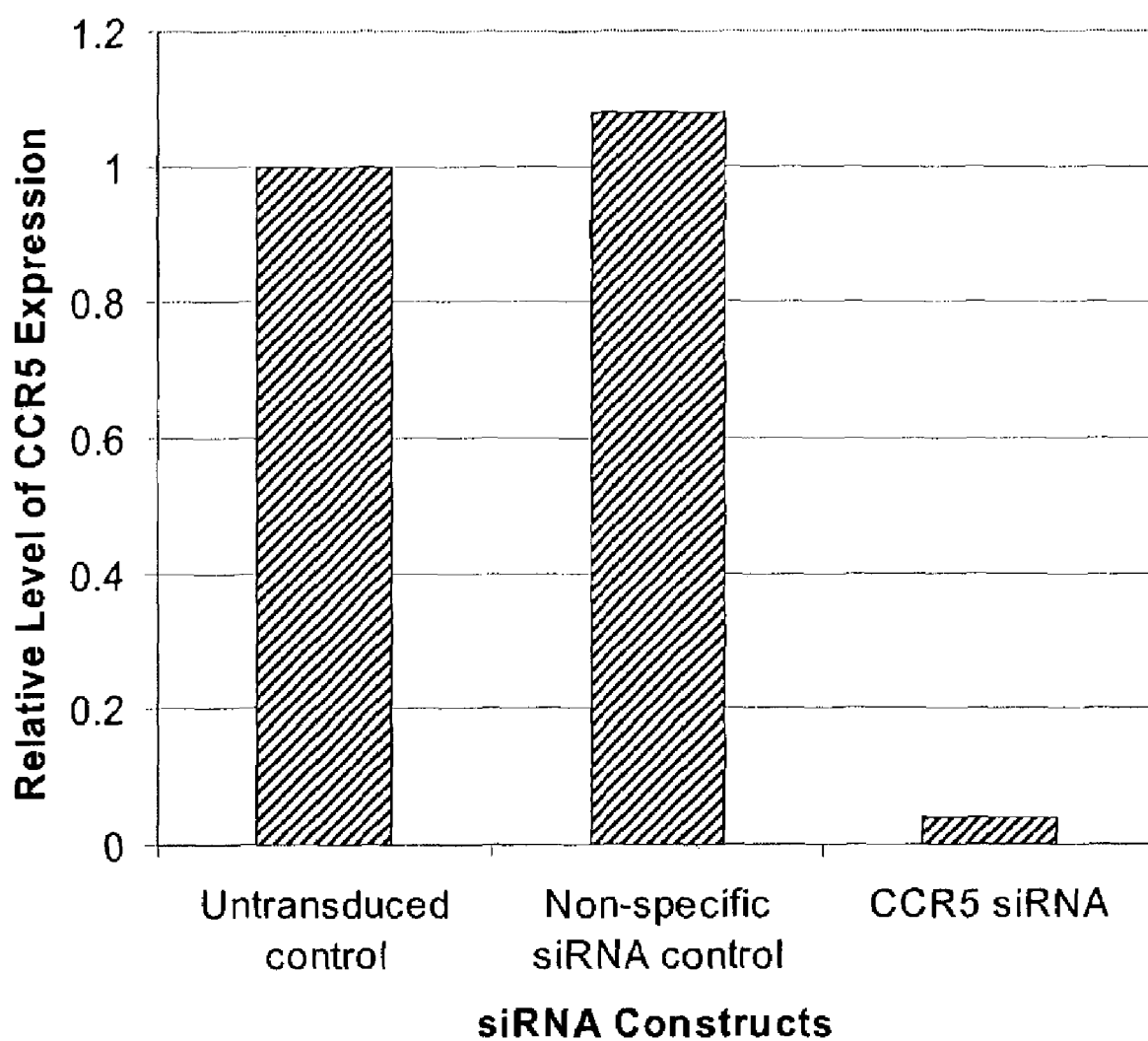
FIG. 11. A anti-human CCR5 specific siRNA encoded by a lentiviral vector can efficiently suppress the expression of CCR5 in transduced human cells. Cell surface expression of CCR5 on transduced or untransduced MAGI-CCR5 (Deng, et al., Nature, 381, 661 (1996)) was measured by flow cytometric analysis (FACS) and the relative expression levels were calculated by mean fluorescence intensity. A non-specific siRNA was also included as a control.

Recombinant retrovirus was prepared from the anti-CCR5 siRNA vector construct as described above. Human MAGI-CCR5 cells (Deng et al., Nature 381:661 (1996)) were infected with the recombinant virus or a retrovirus encoding a non-specific control siRNA and cell surface expression of CCR5 was measured by flow cytometric analysis. Relative expression levels were calculated by mean fluorescence intensity. As can be seen in FIG. 11, the anti-CCR5 siRNA reduced the level of CCR5 expression almost completely, while the non-specific siRNA did not suppress expression at all.

Example 5

Figure 12:
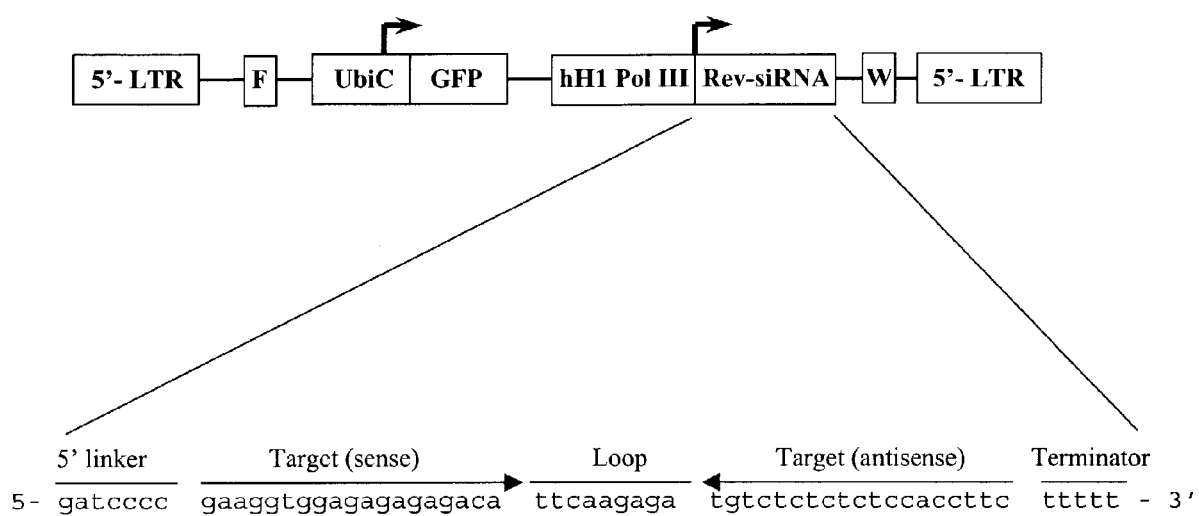
FIG. 12. Schematic illustration of an anti-HIV-1 siRNA encoding lentiviral vector. 5'LTR: an HIV based lentiviral vector 5' LTR; F: an HIV Flap element; a human H1-RNA pol III promoter (−240 to −9); siRNA: a HIV-1 Rev gene specific short hairpin cassette and its structure and detailed sequence are illustrated below. UbiC: an internal human ubiquitinC promoter; GFP: a GFP marker gene driven by UbiC promoter. W: a woodchuck RNA regulatory element. 3'LTR: an HIV based self inactivating lentiviral 3' LTR.

A further anti-HIV-1 siRNA encoding lentiviral vector was constructed, as illustrated in FIG. 12. This vector comprised an RNA coding region encoding an anti-HIV-1 Rev gene specific short hairpin siRNA (SEQ ID NO: 2). The anti-HIV-1 Rev siRNA targeted the 8420 to 8468 region of the Rev coding of HIV-1 (nucleotide coordinate of NL4–3 strain; Salminen et al. Virology 213:80–86 (1995)). The sequence and structure of the siRNA coding region are illustrated in FIG. 12 as well. Expression of the anti-HIV-1 Rev siRNA was driven by a human H1-RNA pol III promoter (−240 to −9; SEQ ID NO: 5).

The ability of the anti-HIV-1 Rev siRNA to suppress HIV transcription in human cells was measured. The transcriptional activity of HIV-1 was measured based on the activity of a firefly luciferase reporter gene inserted at the env/nef region, essentially as described in Li et al. J. Virol. 65:3973 (1991)).

Recombinant retrovirus was prepared from the vector construct as described above and used to infect human cells comprising HIV-1 with the reporter construct. The luciferase activity of untransduced parental cells was arbitrarily set to 1 and the relative HIV transcription levels of the transduced cells were calculated accordingly. A non-specific siRNA was used as a control.

Figure 13:
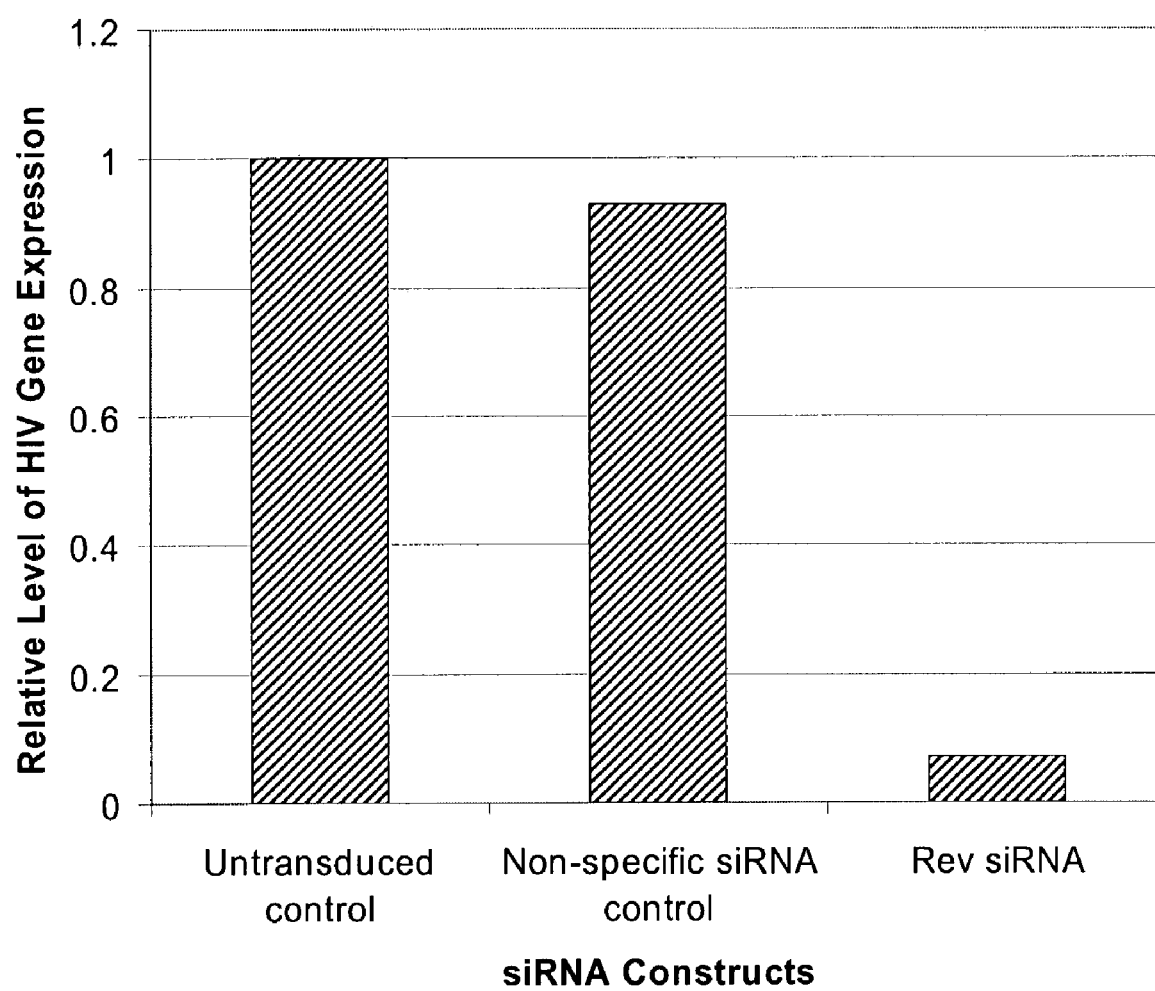
FIG. 13 demonstrates that an anti-HIV-1 Rev gene specific siRNA encoded by a lentiviral vector can efficiently suppress the expression of HIV transcription in human cells. The transcription activity of HIV-1 virus is measured a firefly luciferase reporter gene inserted at the env/nef region (Li, et al J Virol., 65, 3973 (1991)). The luciferase activity of the untransduced parental cells was arbitrarily set to 1 and the relative HIV transcription levels of the transduced cells were calculated accordingly. A non-specific siRNA containing vector was included as a control.

As can be seen in FIG. 13, HIV-1 transcription was significantly suppressed in cells infected with the recombinant retrovirus comprising the anti-HIV-1 Rev siRNA coding region, while the non-specific siRNA had no significant effect.

Example 6

According to this example, an siRNA lentiviral construct against the HIV genome is constructed by insertion of an siRNA expression cassette into the Pac site of HC-FUGW vector. HC-FUGW vector contains a GFP marker gene driven by human Ubiquitin promoter for tracking transduction events. The vector also contains an HIV DNA Flap element to improve the virus titers, and WPRE for high level expression of viral genes. The siRNA expression cassette is composed of a pol III promoter and a small hairpin RNA coding region followed by a pol III terminator site. The pol III promoter is derived from −240 to −8 region of human H1-RNA promoter and is connected to the downstream RNA coding region through a 7 base pair linker sequence to ensure that the transcription is precisely initiated at the first nucleotide of the RNA coding sequence. The small hairpin RNA coding region contains a 21 nt sequence corresponding to a region of the CCR5 coding sequence and the 21 nt perfect reverse complementary sequence separated by a 4 nt loop region. The terminator is comprised of 5 consecutive thymidine residues linked immediately downstream of the RNA coding sequence.

The retroviral construct is used to transfect a packaging cell line (HEK293 cells) along with a helper virus plasmid and VSVg expression plasmid. The recombinant viral particles are recovered.

CD34-positive hematopoietic stem cells are isolated from a patient's bone marrow using a immunomagnetic approach (see, for example, Choi et al.(1995) Blood 85:402–413; Fehse et al. (1997) Human Gene Therapy 8:1815–1824; Di Nicola et al.(1996) Bone Marrow Transplant. 18:1117–1121; Servida et al.(1996) Stem Cells 14:430–438; de Wynter et al.(1995) Stem Cells 13:524–532; Ye et al.(1996) Bone Marrow Transplant. 18:997–1008. ). The cells are cultured and treated with the recombinant virus particles. The infected cells are sorted by FACS based on expression of GFP. Those cells expressing GFP are reintroduced into a patient by injection.

Example 7

Figure 14:
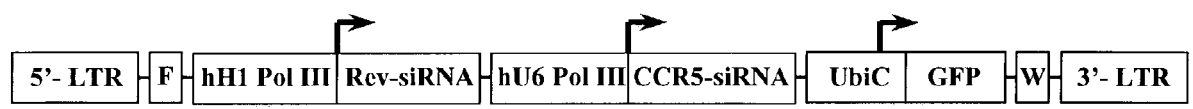
FIG. 14 shows a schematic diagram of a bivalent retroviral vector carrying both anti-HIV Rev and anti-human CCR siRNA expression cassettes. Symbols are the same as depicted in the previous figures.

According to this example, an siRNA lentiviral construct against the HIV genome is constructed by insertion of an siRNA expression cassette into the PacI site of HC-FUGW vector. The siRNA expression cassette comprises a human H1 promoter operatively linked to an RNA coding region encoding an anti-HIV-1 Rev gene specific short hairpin siRNA. The siRNA expression cassette additionally comprises a pol III promoter operatively linked to a small anti-CCR5 hairpin RNA. The retroviral construct is illustrated in FIG. 14.

The retroviral construct is used to transfect a packaging cell line (HEK293 cells) along with a helper virus plasmid and VSVg expression plasmid. The recombinant viral particles are recovered.

CD34-positive hematopoietic stem cells are isolated from a patient's bone marrow using a immunomagnetic approach (see, for example, Choi et al.(1995) Blood 85:402–413; Fehse et al. (1997) Human Gene Therapy 8:1815–1824; Di Nicola et al.(1996) Bone Marrow Transplant. 18:1117–1121; Servida et al.(1996) Stem Cells 14:430–438; de Wynter et al.(1995) Stem Cells 13:524–532; Ye et al.(1996) Bone Marrow Transplant. 18:997–1008. ). The cells are cultured and treated with the recombinant virus particles. The infected cells are sorted by FACS based on expression of GFP. Those cells expressing GFP are reintroduced into a patient by injection.

Example 8

Virus production from the lentiviral vector carrying the anti-HIV-1 Rev siRNA expression cassette, as described in Example 6, was tested by co-transfecting 293T cells with the lentiviral vector, a packaging plasmid (pRSV-Rev; Dull, T. et al. J Virol. 72(11): 8463–8471 (1998)) comprising the wild type Rev sequence (SEQ ID NO: 11) and a VSVg expression plasmid. The ability to increase virus production was tested by use of a mutant form of the pRSV-Rev packaging plasmid that is resistant to Rev-siRNA mediated degradation. In this plasmid the mutant Rev nucleotide sequence (SEQ ID NO: 12) comprises two silent mutations that make the Rev mRNA resistant to siRNA mediated degradation, but do not alter the amino acid sequence. In addition, the effect on virus production of expression of one or more siRNA that inhibit RNA interference was tested.

Figure 15:
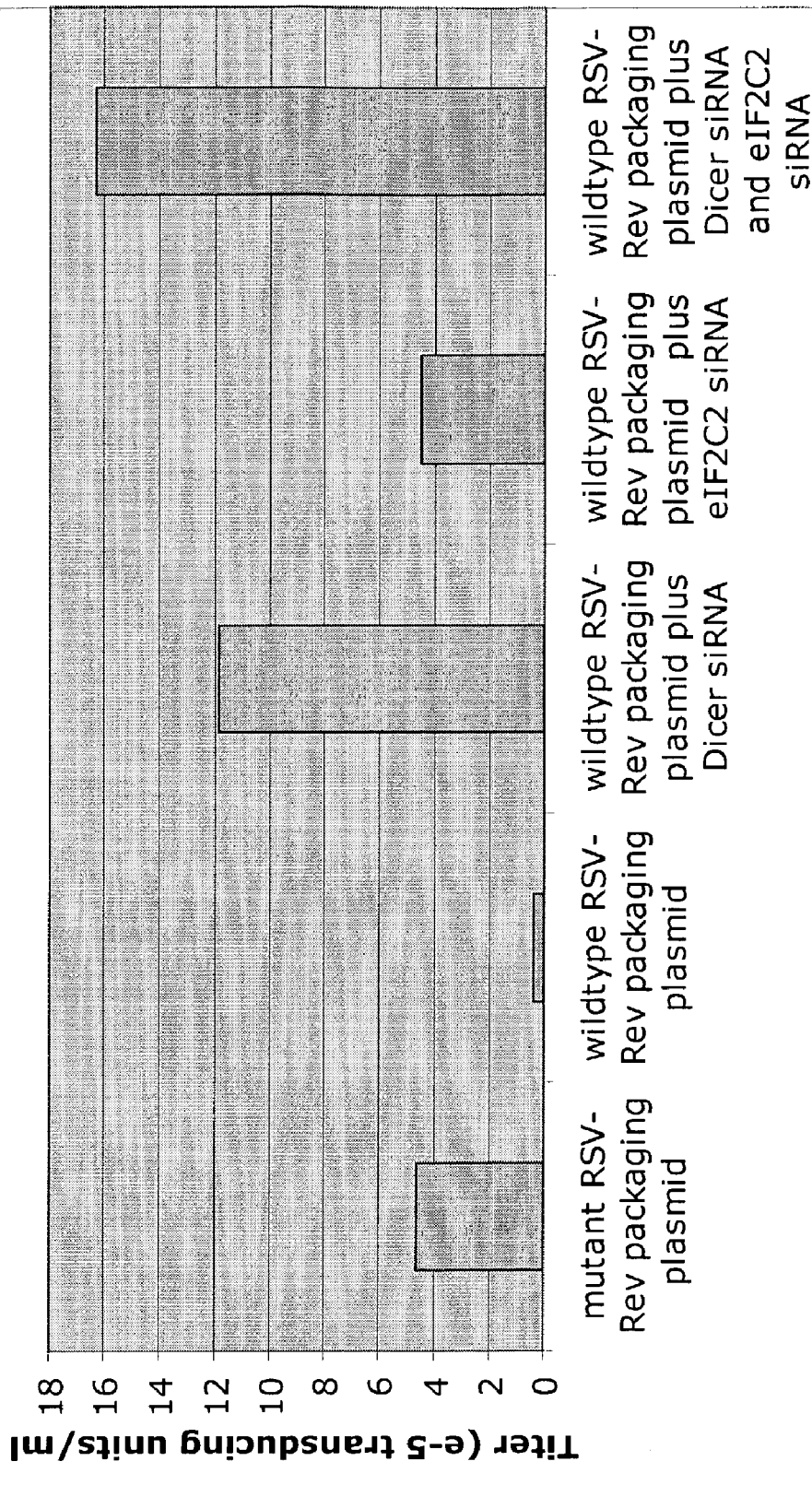
FIG. 15 shows virus production from lentiviral vector comprising the anti-Rev siRNA expression cassette after cotransfection with wild type pRSV-Rev packaging plasmid, mutant pRSV-Rev that is resistant to Rev-siRNA mediated degradation, or wild type pRSV-Rev in the presence of anti-Dicer, anti-eIF2C2 or anti-Dicer and anti-eIF2C2 siRNAs.

Cells were cotransfected with either wild-type pRSV-Rev alone, the mutant form of pRSV-Rev, wild-type pRSV-Rev plus a plasmid that drives expression of anti-Dicer-1 siRNA (SEQ ID NO: 8), wild-type pRSV-Rev plus a plasmid that drives expression of anti-eIF2C2 siRNA (SEQ ID NO: 9), or the wild-type pRSV-Rev plus a plasmid that drives expression of anti-Dicer siRNA and anti-eIF2C2 siRNA. Anti-Dicer-1 and anti-eIF2C2 siRNA expression was under the control of the human H1-RNA pol III promoter (−241 to −9; SEQ ID NO: 10). As can be seen in Table 1 and FIG. 15, virus titer was greatest from 293T cells transfected with pRSV-Rev in the presence of anti-Dicer siRNA and the combination of anti-Dicer siRNA and anti-eIF2C2 siRNA.

TABLE 1

| Transfection | Titer (e-5 TU/ml) |
| --- | --- |
| wild-type pRSV-Rev plasmid | 0.34 |
| mutant pRSV-Rev packaging plasmid | 4.6 |
| wild-type pRSV-Rev plasmid + anti-Dicer-1 siRNA | 11.8 |
| wild-type pRSV-Rev plasmid + anti-eIF2C2 siRNA | 4.5 |
| wild-type pRSV-Rev plasmid + anti-Dicer-1 siRNA + anti-eIF2C2 siRNA | 16.3 |

A packaging cell line that stably expresses both anti-Dicer-1 (SEQ ID NO: 8) and anti-eIF2C2 (SEQ ID NO: 9) siRNAs was created. 293 cells were transfected with a pcDNA4 (Invitrogen) vector comprising anti-eIF2C2 and anti-dicer expression cassettes as well as a Zeocin resistance gene for drug selection.

What is claimed is:

1. A method of producing recombinant retrovirus comprising:
   transfecting a packaging cell with a first retroviral construct comprising a first RNA coding region encoding a first siRNA, wherein expression of the first RNA coding region results in the down regulation of expression of a first target gene comprising a target sequence; and
   transfecting the packaging cell with a second retroviral construct comprising a second RNA coding region encoding a second siRNA targeting a second target gene,
   wherein expression of the second RNA coding region mediates RNA interference in the packaging cell, which second target gene is selected from the group consisting of Dicer-1 and eIF2C2, thereby inhibiting RNA interference in the packaging cell.

2. The method of claim 1 wherein the first target gene is selected from the group consisting of genes within the genome of a pathogenic virus, cellular genes that are involved in the lifecycle of a pathogenic virus, and genes that mediate a disease or disorder.

3. The method of claim 2 wherein the first target gene is a gene within the human immunodeficiency virus (HIV) genome.

4. The method of claim 3 wherein the first target gene is selected from the group consisting of gag, pol and rev.

5. The method of claim 4 wherein the first target gene is rev.

6. The method of claim 1 wherein the second RNA coding region comprises the sequence of SEQ ID NO: 8.

7. The method of claim 1 wherein the second RNA coding region comprises the sequence of SEQ ID NO: 9.

8. The method of claim 1 wherein the first and second RNA coding regions encode RNA molecule having a sense region, an antisense region and a loop region, and wherein the sense region is complementary to the antisense region.

9. The method of claim 1 additionally comprising co-transfecting the packaging cell line with:
   c) a third vector comprising a third RNA coding region; wherein expression of the third RNA coding region results in down regulation of expression of a third target gene wherein the third target gene is selected from the group consisting of Dicer-1 and eIF2C2, thereby inhibiting RNA interference in the packaging cell.

10. The method of claim 1 wherein said packaging cell line is a 293 cell line.

11. The method of claim 1 wherein the recombinant retrovirus is pseudotyped.

12. The method of claim 11 wherein the recombinant retrovirus is pseudotyped with the vesicular stomatitits virus envelope glycoprotein.

13. The method of claim 1 wherein the first target gene is necessary for the life cycle of a virus.

14. The method of claim 13 wherein the target gene is selected from the group consisting of Rev, Gag and Pol.

15. The method of claim 1 wherein the first target gene is selected from the group consisting LTRs, TAR, RRE, Ψ, att, pbs, ppt.

16. The method of claim 1 wherein the second siRNA is transiently expressed within the packaging cell.

17. The method of claim 1 wherein the second siRNA is stably expressed within the packaging cell.

* * * * *

UNITED STATES PATENT AND TRADEMARK OFFICE
CERTIFICATE OF CORRECTION

PATENT NO. : 7,195,916 B2 Page 1 of 1
APPLICATION NO. : 10/319341
DATED : March 27, 2007
INVENTOR(S) : Xiao-Feng Qin and David Baltimore It is certified that error appears in the above-identified patent and that said Letters Patent is hereby corrected as shown below:

On the first page, Col. 2, Abstract, line 8, please delete "that." and insert --gene involved in the lifecycle of a pathogenic virus.--.

In Col. 3, line 38, after "pol III" pelase delete " . ".

In Col. 3, line 56, before "retroviral" pelase delete " : ".

In Col. 7, line 13, after "vector." please delete "5." and insert --5--, therefor.

In Col. 42, line 7, claim 9 please delete "c)".

Signed and Sealed this

Thirty-first Day of July, 2007

JON W. DUDAS
*Director of the United States Patent and Trademark Office*

UNITED STATES PATENT AND TRADEMARK OFFICE
CERTIFICATE OF CORRECTION

PATENT NO. : 7,195,916 B2  
APPLICATION NO. : 10/319341  
DATED : March 27, 2007  
INVENTOR(S) : Xiao-Feng Qin et al.

Page 1 of 1

It is certified that error appears in the above-identified patent and that said Letters Patent is hereby corrected as shown below:

On the Title page, under section (75) Inventors, please add --Irvin S.Y. Chen, Palos Verdes Estates, CA (US)-- and --Dong Sung An, Los Angeles, CA (US)--

On the Title page, under section (73) Assignee, please add --The Regents of the University of California, Oakland, CA (US)--

Signed and Sealed this

Fourth Day of May, 2010

David J. Kappos  
*Director of the United States Patent and Trademark Office*

UNITED STATES PATENT AND TRADEMARK OFFICE
CERTIFICATE OF CORRECTION

PATENT NO.       : 7,195,916 B2
APPLICATION NO.  : 10/319341
DATED            : March 27, 2007
INVENTOR(S)      : Qin et al.

It is certified that error appears in the above-identified patent and that said Letters Patent is hereby corrected as shown below:

At column 1, line 19, under the section entitled "GOVERNMENTAL SUPPORT," after "Grant" please delete "Number" and insert --Numbers-- therefore.

On column 1, line 19, under the section entitled "GOVERNMENTAL SUPPORT," after "GM39458" and before "awarded" please insert --, AI39975 and AI55281--.

Signed and Sealed this
Twenty-sixth Day of July, 2011

David J. Kappos
*Director of the United States Patent and Trademark Office*